United States Patent [19]
Wiegers et al.

[11] Patent Number: 5,783,724
[45] Date of Patent: Jul. 21, 1998

[54] ALLYL ESTERS OF 2-NORBORNANE ACRYLIC ACIDS AND 2-NORBORNYLIDENE PROPIONIC AICDS AND PERFUMERY USES THEREOF

[75] Inventors: Wilhelmus Johannes Wiegers, Red Bank; Marie R. Hanna, Keyport, both of N.J.

[73] Assignee: International Flavors & Fragrances Inc., New York, N.Y.

[21] Appl. No.: 812,278

[22] Filed: Mar. 6, 1997

Related U.S. Application Data

[62] Division of Ser. No. 450,823, May 25, 1995.
[51] Int. Cl.[6] .................................. C07C 67/08
[52] U.S. Cl. ................... 560/120; 562/502; 562/595
[58] Field of Search ................... 560/120; 562/502, 562/595

[56] References Cited

U.S. PATENT DOCUMENTS

| | | | |
|---|---|---|---|
| 4,319,036 | 3/1982 | Klemarczyk et al. | 512/22 |
| 4,728,747 | 3/1988 | Hoffman et al. | 512/22 |

FOREIGN PATENT DOCUMENTS

| | | | |
|---|---|---|---|
| 2163770 | 7/1973 | Germany | 512/22 |
| 2517620 | 11/1976 | Germany | 512/22 |

*Primary Examiner*—James H. Reamer
*Attorney, Agent, or Firm*—Arthur L. Liberman

[57] ABSTRACT

Described are allyl esters of 2-norbornane acrylic acids and 2-norbornylidene propionic acids defined according to the generic structure:

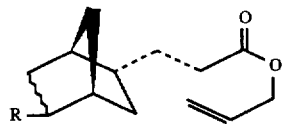

wherein the wavy line represents a carbon-carbon single bond or a carbon-carbon double bond; wherein one of the dashed lines is carbon-carbon single bond and the other of the dashed lines is a carbon-carbon double bond; and wherein R represents methyl or hydrogen; as well as methods for augmenting or enhancing the aroma of consumable materials including perfumes, colognes and perfumed articles.

2 Claims, 25 Drawing Sheets

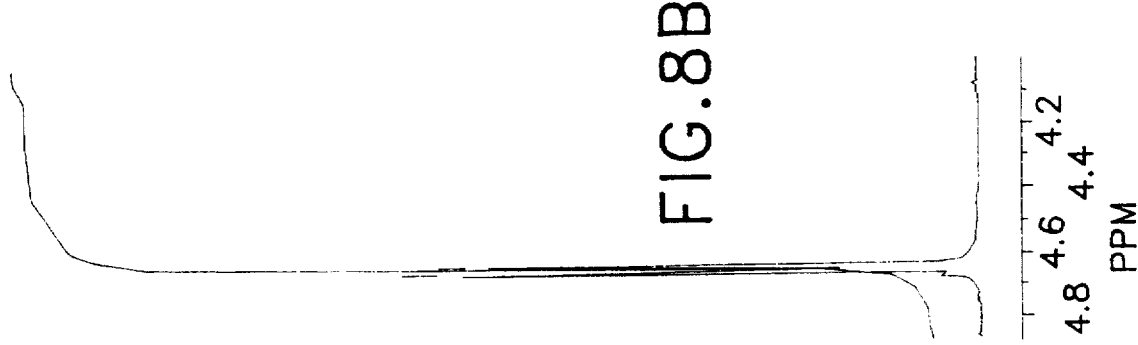
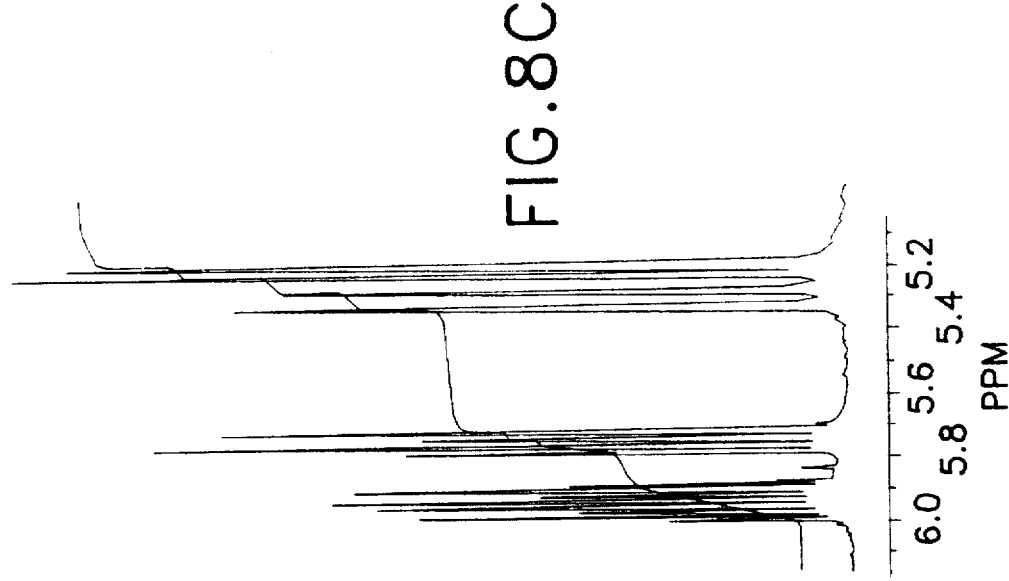
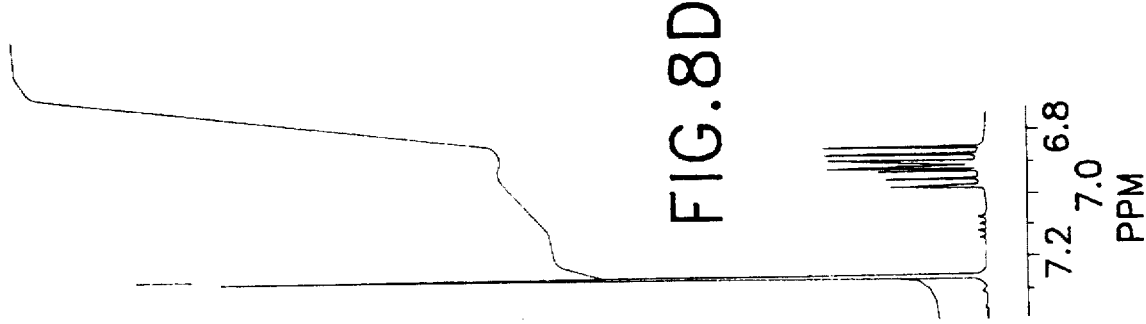

5,783,724

ALLYL ESTERS OF 2-NORBORNANE ACRYLIC ACIDS AND 2-NORBORNYLIDENE PROPIONIC AICDS AND PERFUMERY USES THEREOF

This is a Divisional of application Ser. No. 08/450,823 filed on May 25, 1995.

BACKGROUND OF THE INVENTION

The instant invention provides allyl esters of 2-norbornane acrylic acids and 2-norbornylidene propionic acids defined according to the structure:

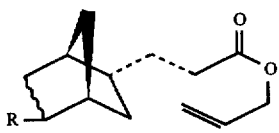

wherein the wavy line represents a carbon-carbon single bond or a carbon-carbon double bond; and wherein one of the dashed lines is carbon-carbon single bond and the other of the dashed lines is a carbon-carbon double bond and wherein R represents methyl or hydrogen and uses thereof for augmenting, enhancing or imparting aromas in or to perfume compositions, colognes and perfumed articles (e.g., perfumed plastics, solid or liquid anionic, cationic, nonionic or zwitterionic detergents, fabric softener compositions or dryer added fabric softener articles).

Inexpensive compositions of matter which can provide coconut, pineapple-like, fruity, lactonic, coumarin-like, sweet, animalic and sweaty aromas with floral undertones and pineapple, coconut, galbanum, sweet, herbaceous, oolong tea-like, sweaty and animalic topnotes are highly desirable in the art of perfumery. Many of the natural materials which provide such fragrances and contribute such desired nuances to perfumery compositions as well as perfumed articles including solid or liquid anionic, cationic, nonionic or zwitterionic detergents, perfumed polymers, fabric softener compositions, fabric softener articles, hair preparations, cosmetic powders and the like are high in cost, vary in quality from one batch to another and/or are generally subject to the usual variations of natural products.

Thus, the search for materials which can provide more refined coconut, pineapple-like, fruity, lactonic, coumarin-like, sweet, animalic and sweaty aromas has been difficult and relatively costly in the areas of both natural products and synthetic products.

2-Norbornyl carboxylic acid esters are known in the prior art for their uses in perfumery. Thus, German Offenlegungsschrift 2,163,770 published on Jul. 5, 1973 discloses the use of compounds defined according to the structure:

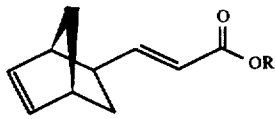

wherein R represents $C_1$–$C_5$ alkyl in perfumery. German Offenlegungsschrift 2,163,770 is abstracted at *Chemical Abstracts*, Volume 79 (1973) 78231b.

German Offenlegungsschrift 2,517,620 published on Nov. 4, 1976 discloses uses of the compounds having the structures:

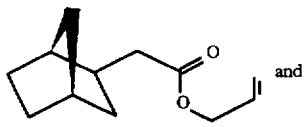

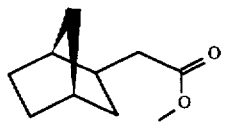

in perfumery. German Offenlegungsschrift 2,517,620 is abstracted at *Chemical Abstracts*, Volume 86 (1977) 72035p.

Mixtures of compounds having the structures:

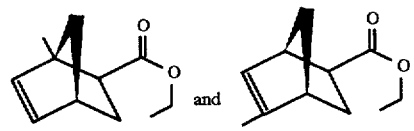

as well as mixtures of compounds having the structures:

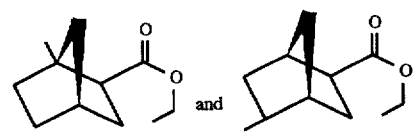

are disclosed by Klemarczyk, et al, U.S. Pat. No. 4,319,036 issued on Mar. 9, 1982.

U.S. Pat. No. 4,728,747 issued on Mar. 1, 1988, Hoffman, et al, discloses compounds having the generic structure:

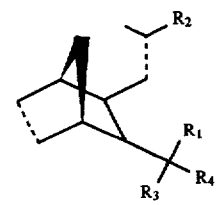

wherein $R_1$ represents $C_1$–$C_3$ alkyl; $R_2$ represents $C_1$–$C_8$ alkyl; $R_3$ and $R_4$, taken together, can be the structure:

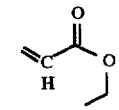

or $R_3$ is hydrogen when $R_4$ is the moiety:

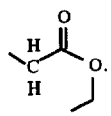

The Hoffman, et al patent actually discloses the genus defined according to the structure:

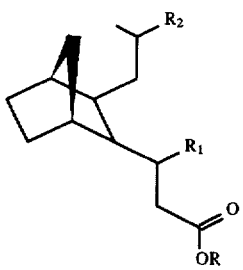

wherein R represents methyl or ethyl; $R_1$ represents $C_1$–$C_3$ alkyl; and $R_2$ represents $C_1$–$C_8$ alkyl.

Although the Hoffman, et al reference does not disclose the following compounds, the following compounds are covered within the Hoffman genus:

(1) the compound having the structure:

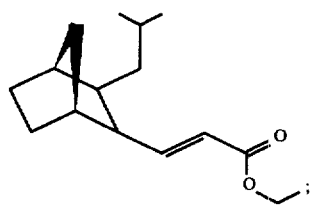

(2) the compound having the structure:

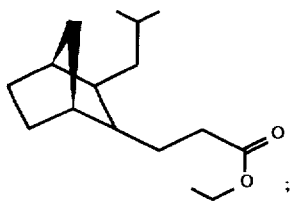

(3) the compound having the structure:

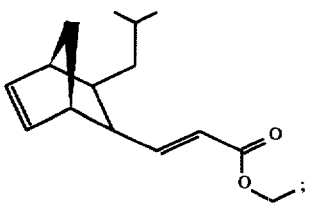

(4) the compound having the structure:

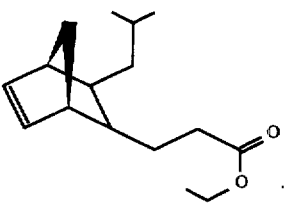

Nothing in the prior art sets forth the allyl esters of 2-norbornane acrylic acids and 2-norbornylidene propionic acids of our invention. Furthermore, nothing in the prior art infers that compounds such as the allyl esters of 2-norbornane acrylic acids and 2-norbornylidene propionic acids of our invention can have the unexpected, unobvious and advantageous perfumery properties insofar as strength, substantivity and quality of fragrance.

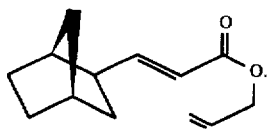

Figure 2:
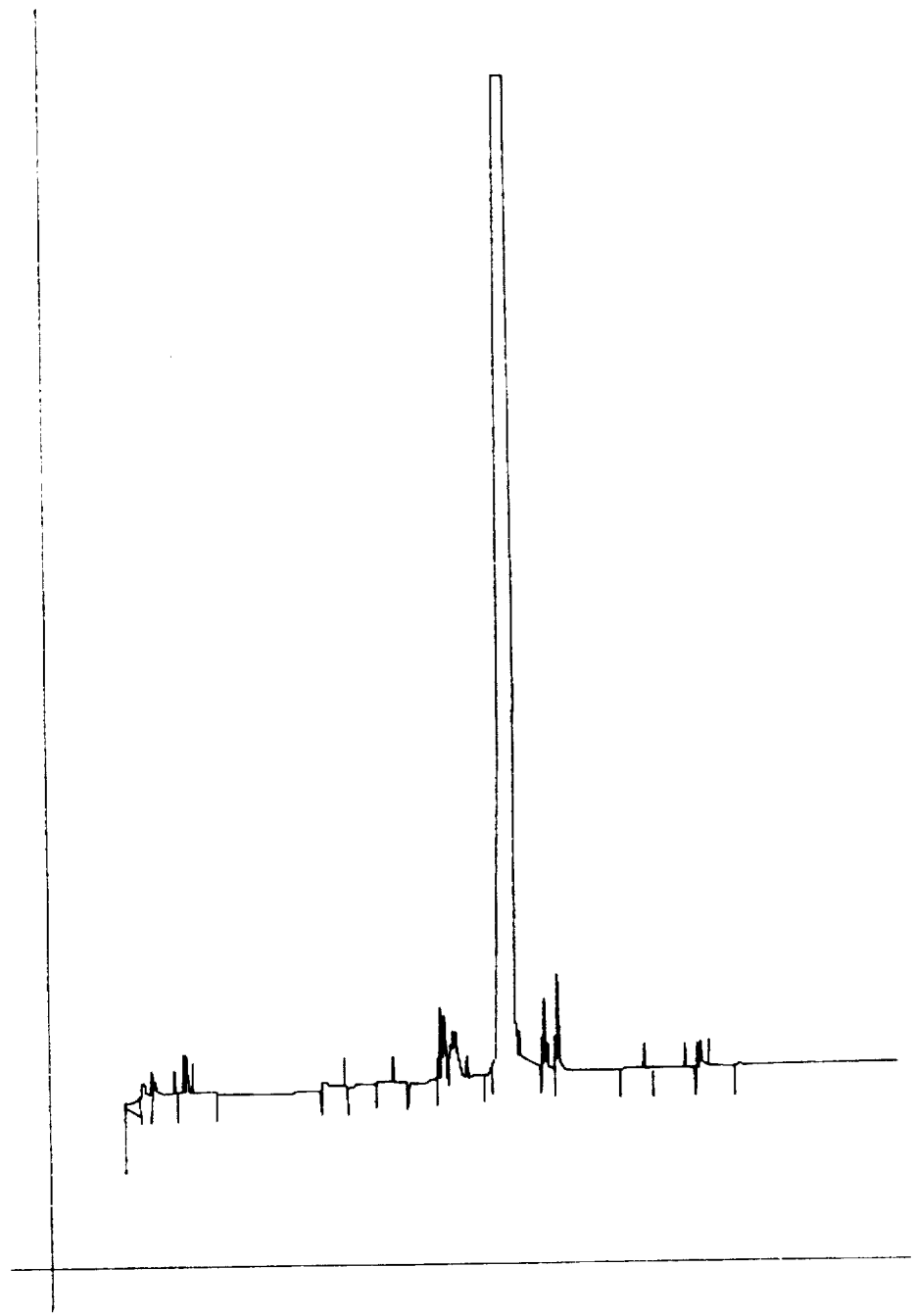

FIG. 2 is the GC spectrum for the "rushed over" distillation product of Example I(B) containing the compound having the structure:

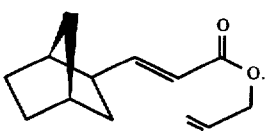

Figure 3:
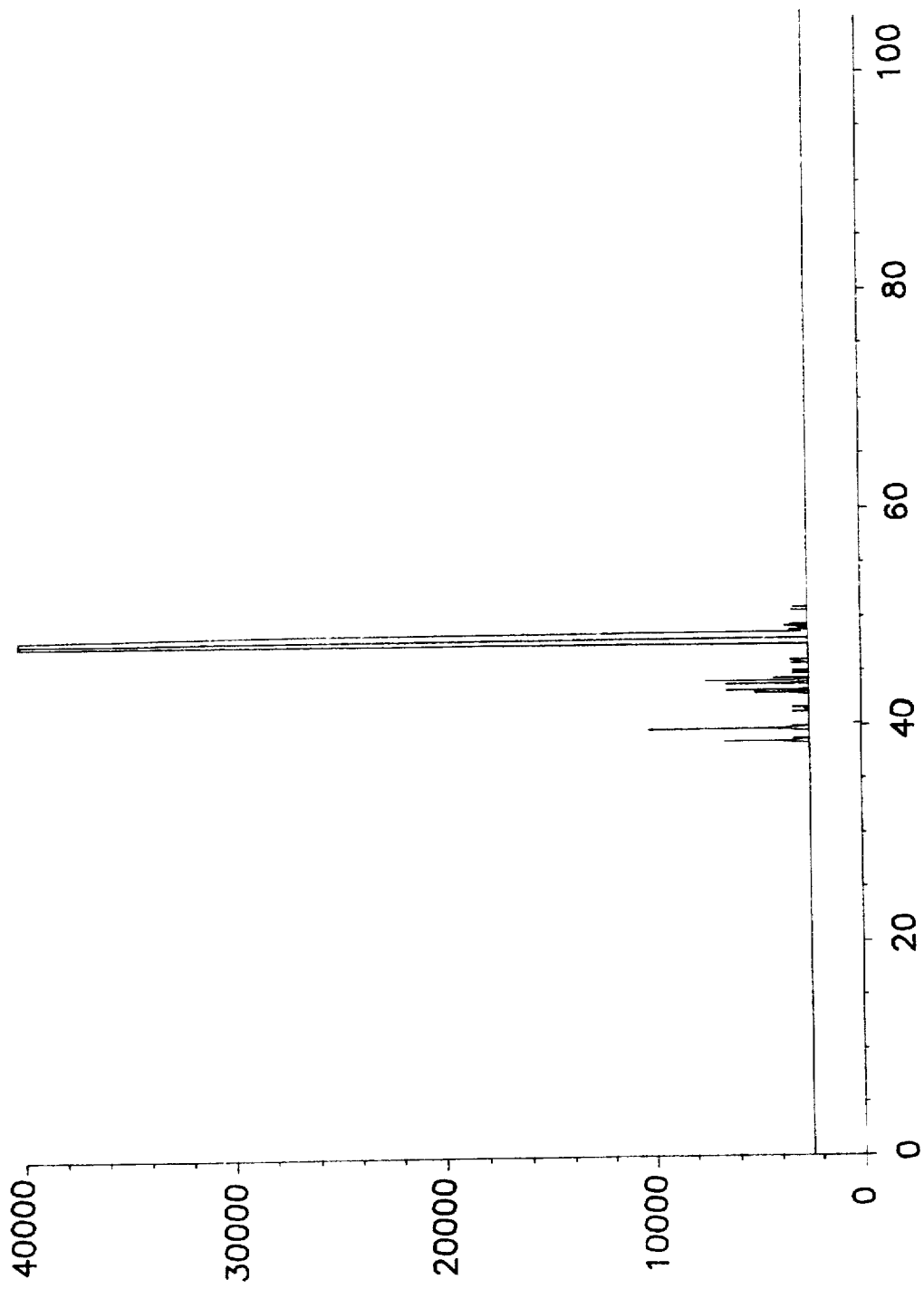

FIG. 3 is the GC spectrum for the reaction product of Example I(B) (crude reaction product).

Figure 4:
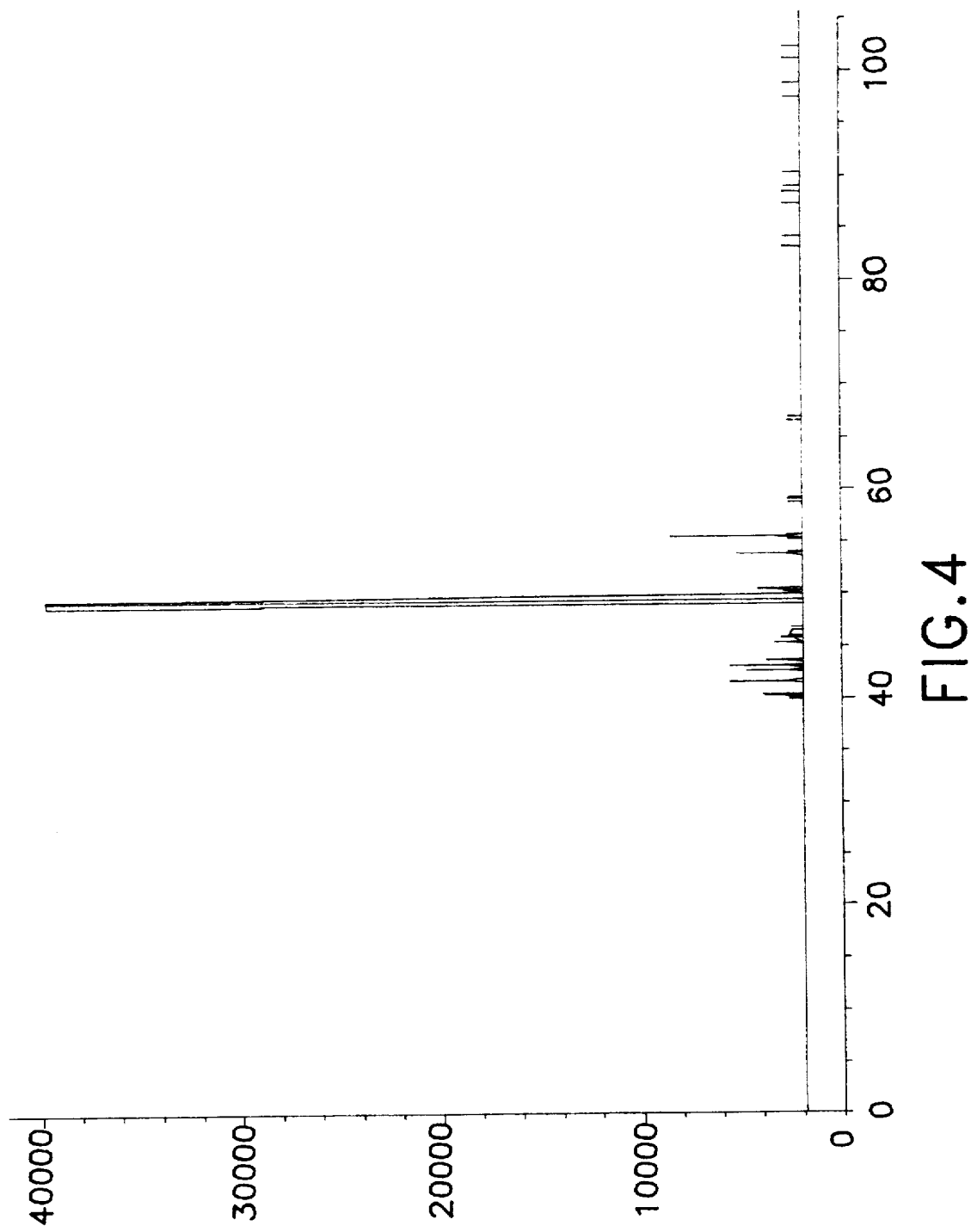

FIG. 4 is another GC spectrum for the crude reaction product of Example I(B).

Figure 5:
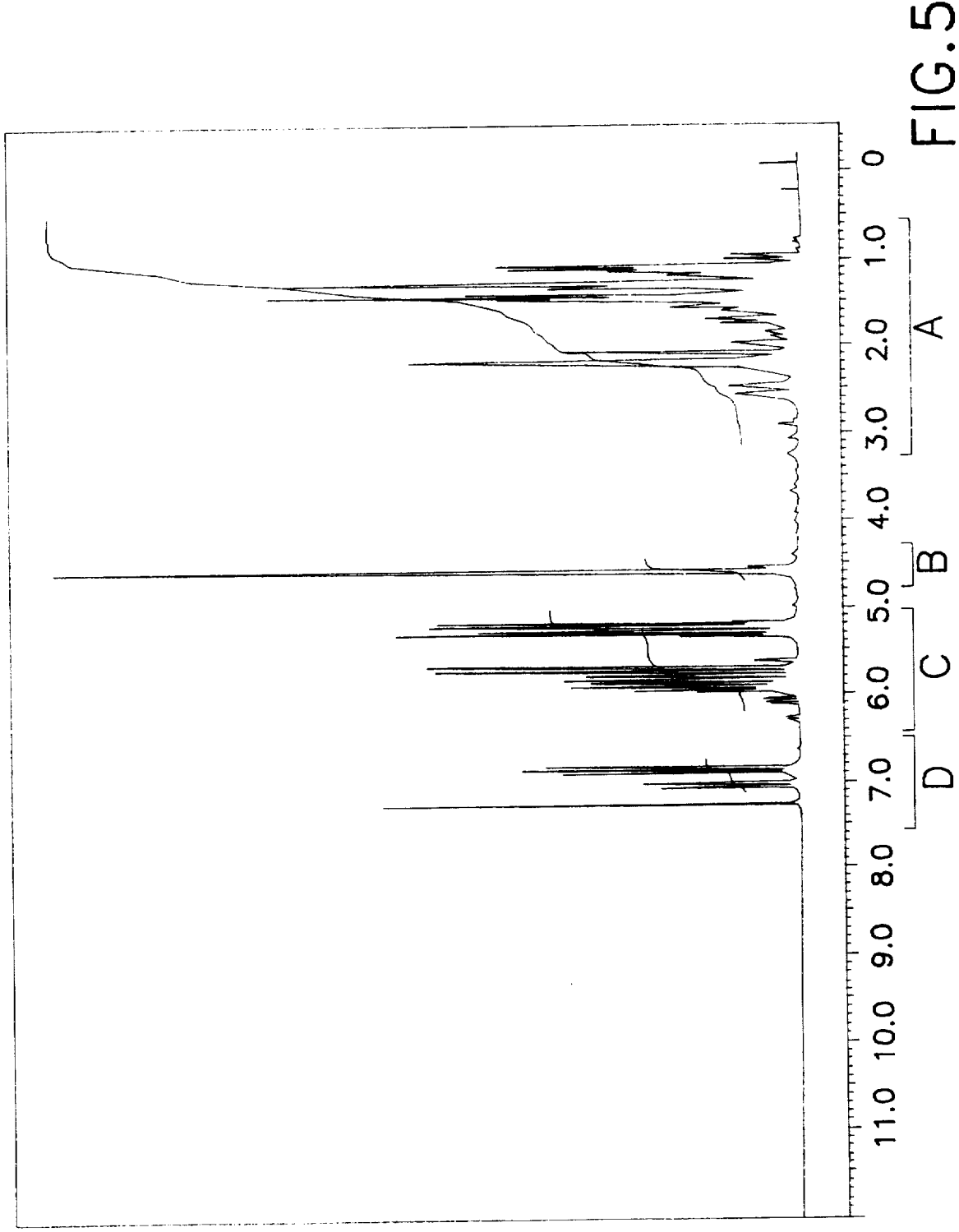

FIG. 5 is the NMR spectrum for the compound having the structure:

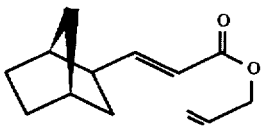

prepared according to Example I(B).

Figure 5A:
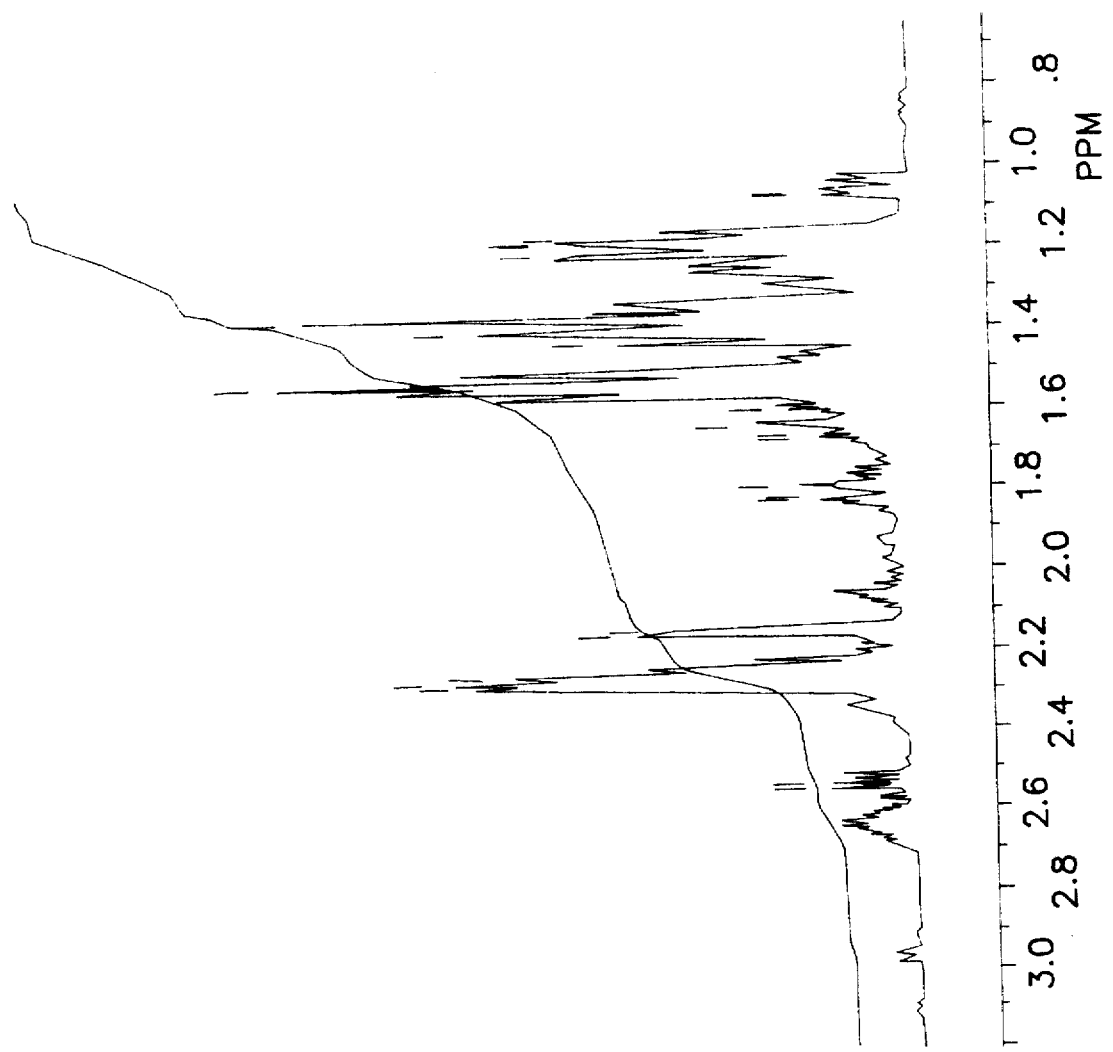

FIG. 5A is an enlargement of section "A" of the NMR spectrum of FIG. 5.

Figure 5B:

FIG. 5B is an enlargement of section "B" of the NMR spectrum of FIG. 5.

Figure 5C:
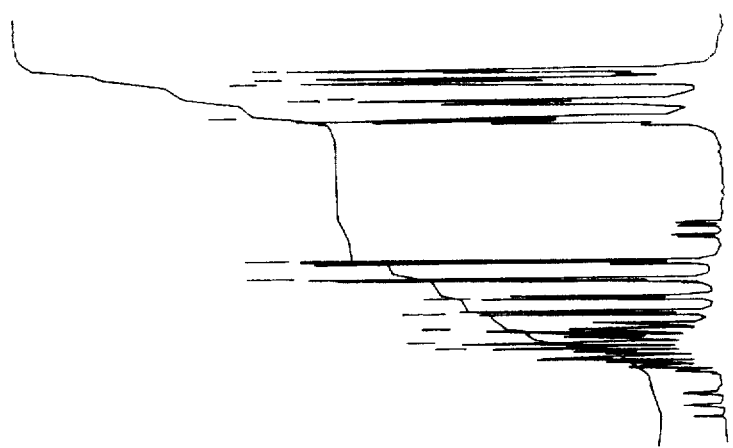

FIG. 5C is an enlargement of section "C" of the NMR spectrum of FIG. 5.

Figure 5D:
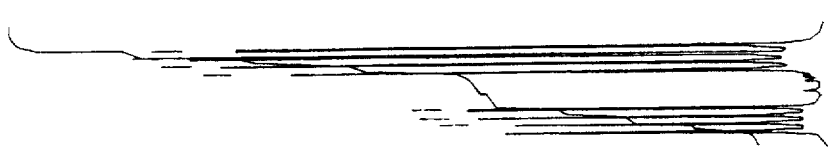

FIG. 5D is an enlargement of section "D" of the NMR spectrum of FIG. 5.

Figure 6:
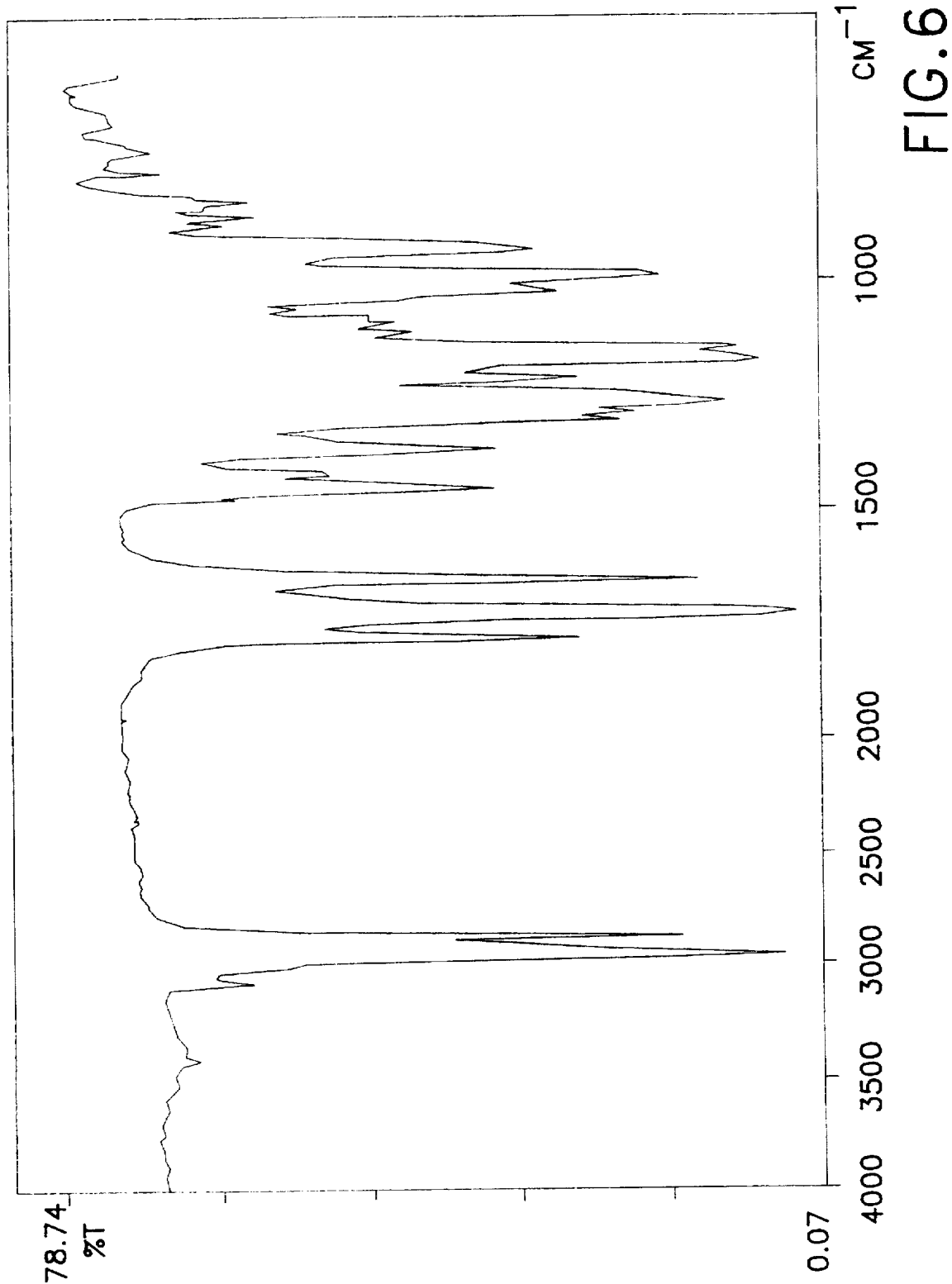

FIG. 6 is the infrared spectrum for the compound having the structure:

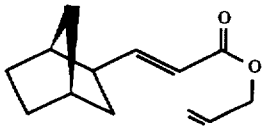

prepared according to Example I(B).

Figure 7:
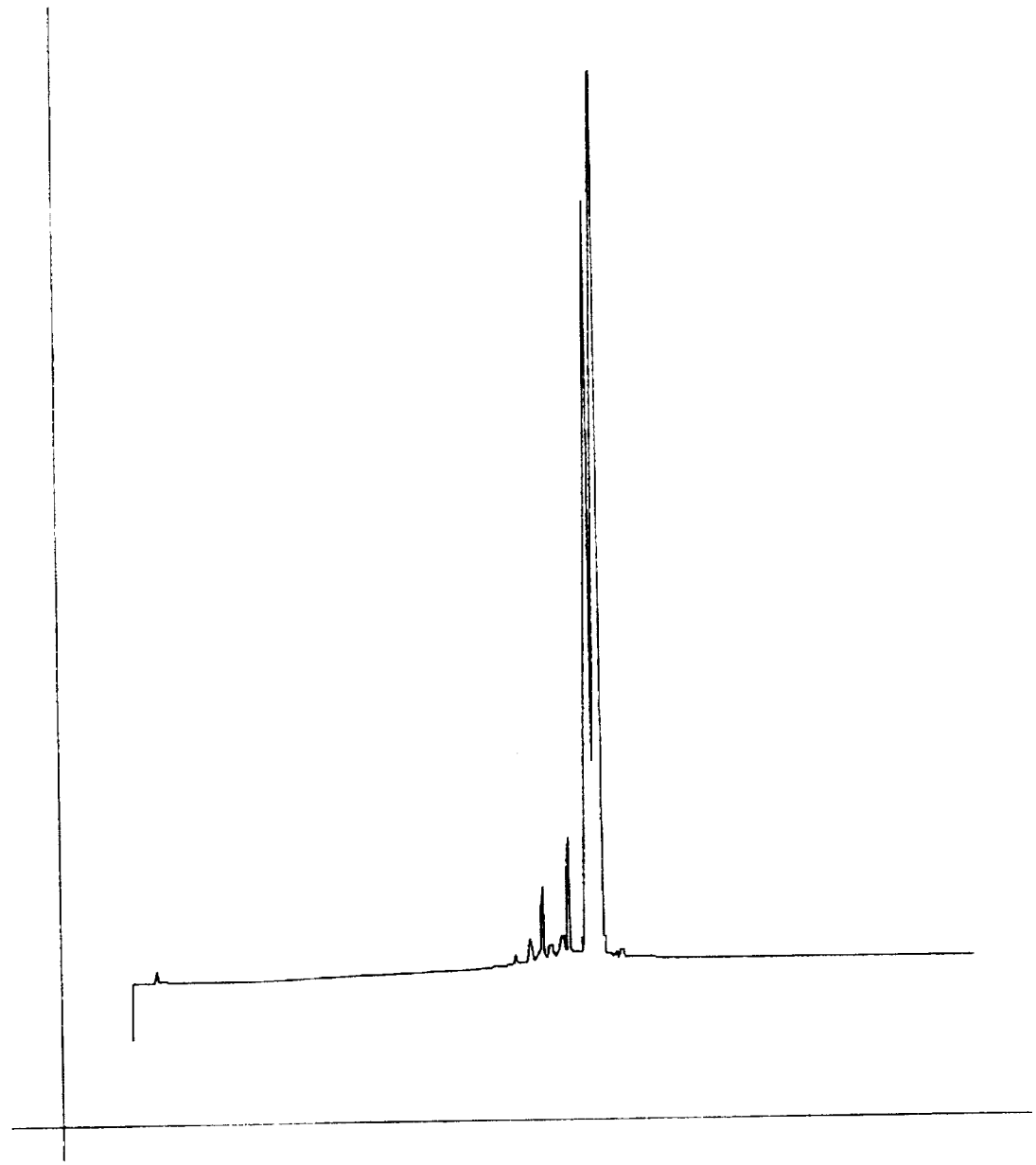

FIG. 7 is the GC spectrum for the reaction product of Example II containing the compound having the structure:

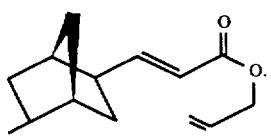

Figure 8:
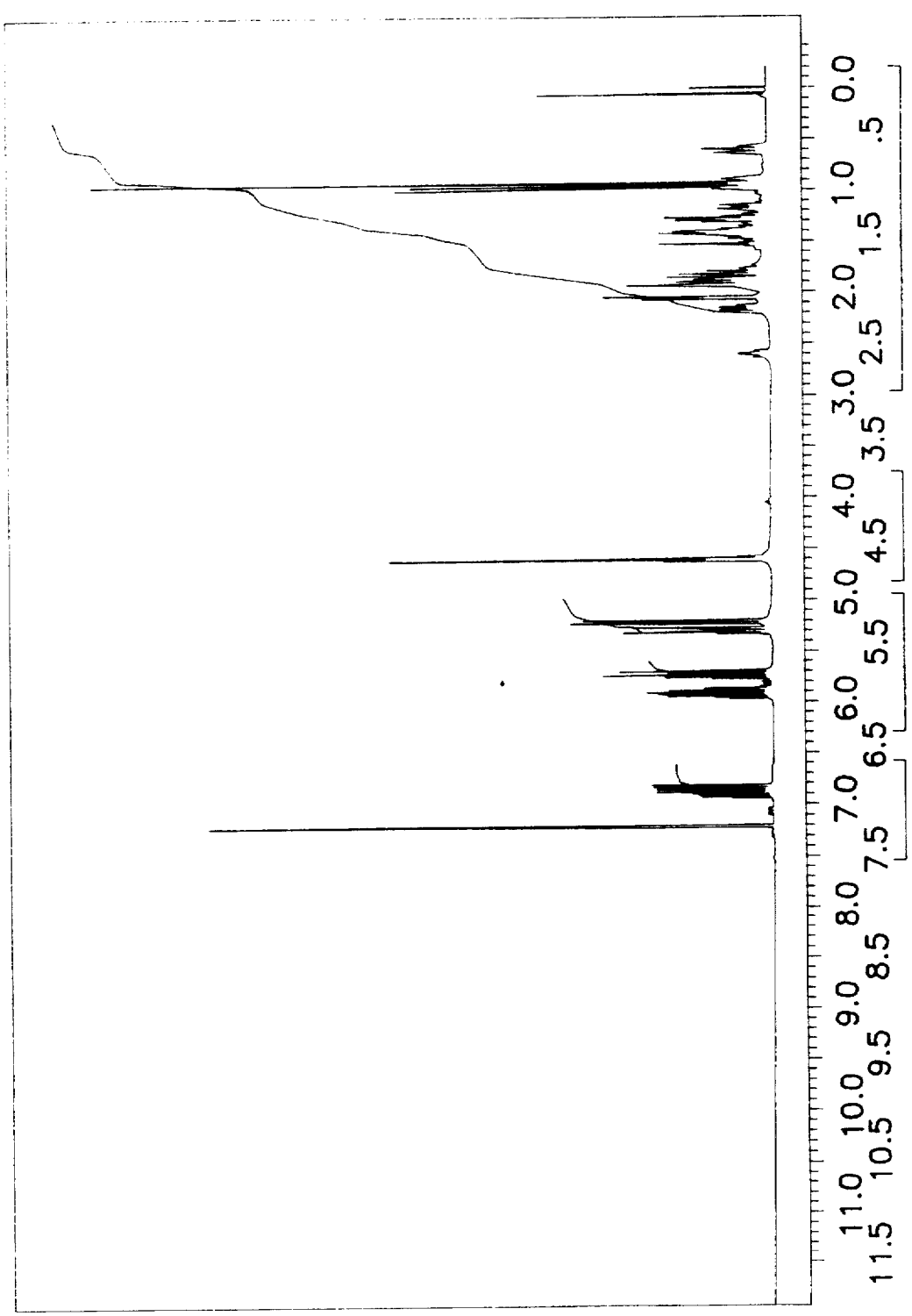

FIG. 8 is the NMR spectrum for the compound having the structure:

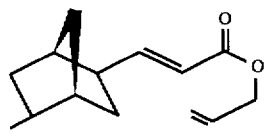

prepared according to Example II.

Figure 8A:
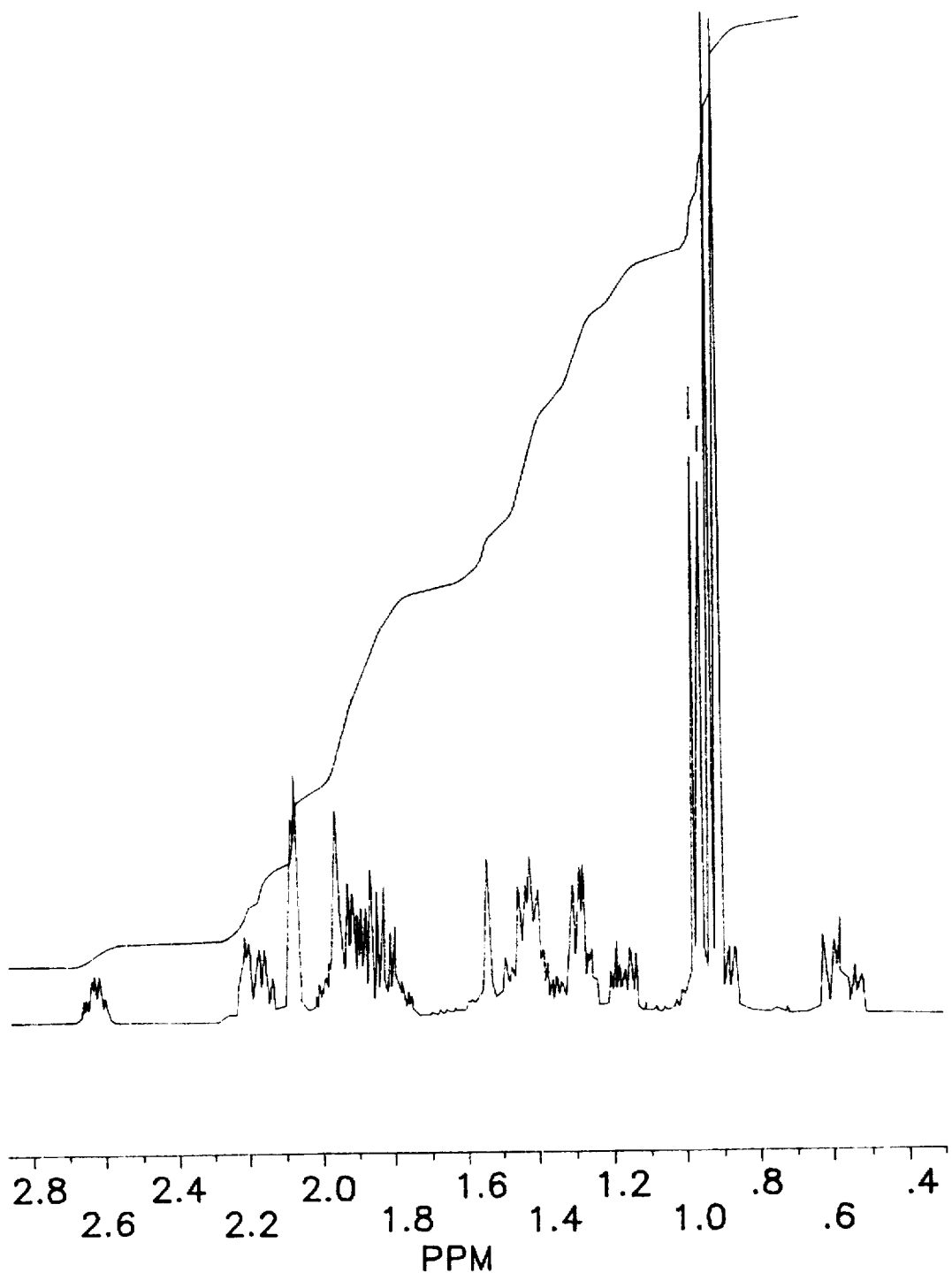
Figure 9:
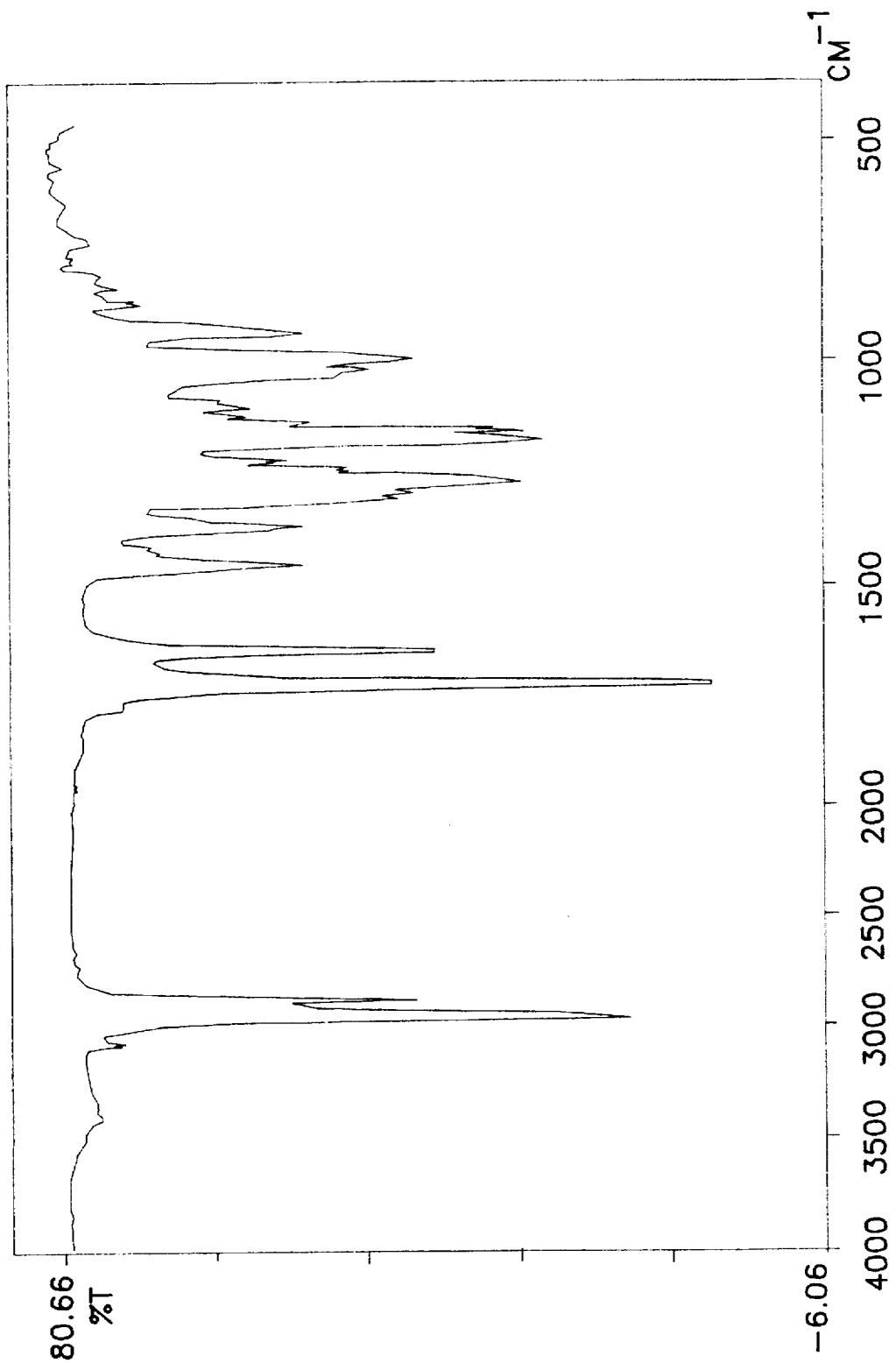

FIG. 8A is an enlargement of section "A" of the NMR spectrum of FIG. 8.
FIG. 8B is an enlargement of section "B" of the NMR spectrum of FIG. 8.
FIG. 8C is an enlargement of section "C" of the NMR spectrum of FIG. 8.
FIG. 8D is an enlargement of section "D" of the NMR spectrum of FIG. 8.
FIG. 9 is the infrared spectrum for the compound a having the structure:

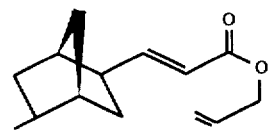

prepared according to Example II.

Figure 10:
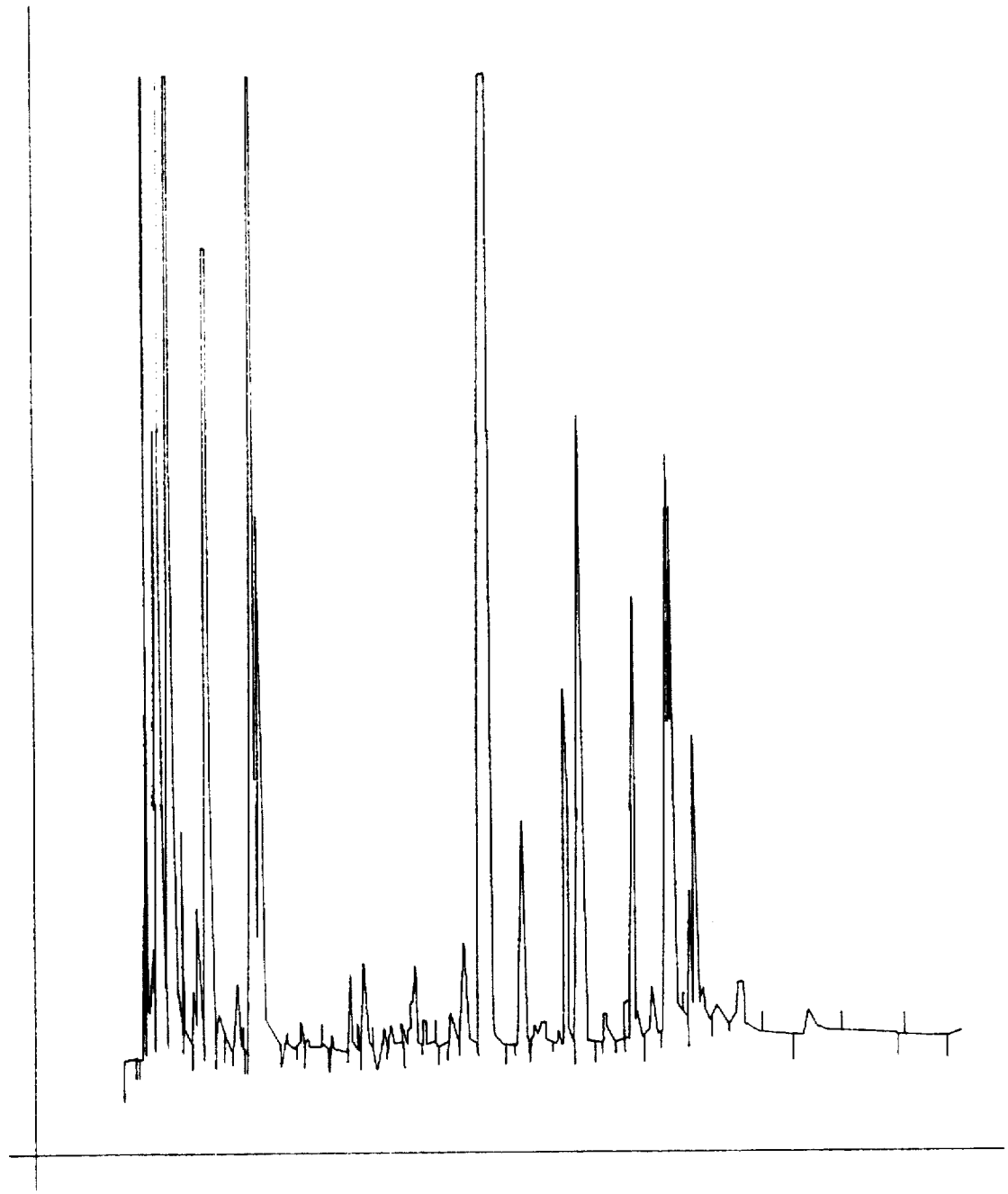

FIG. 10 is the GC spectrum for the crude reaction product of Example III containing the compound having the structure:

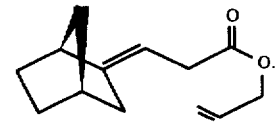

Figure 11:
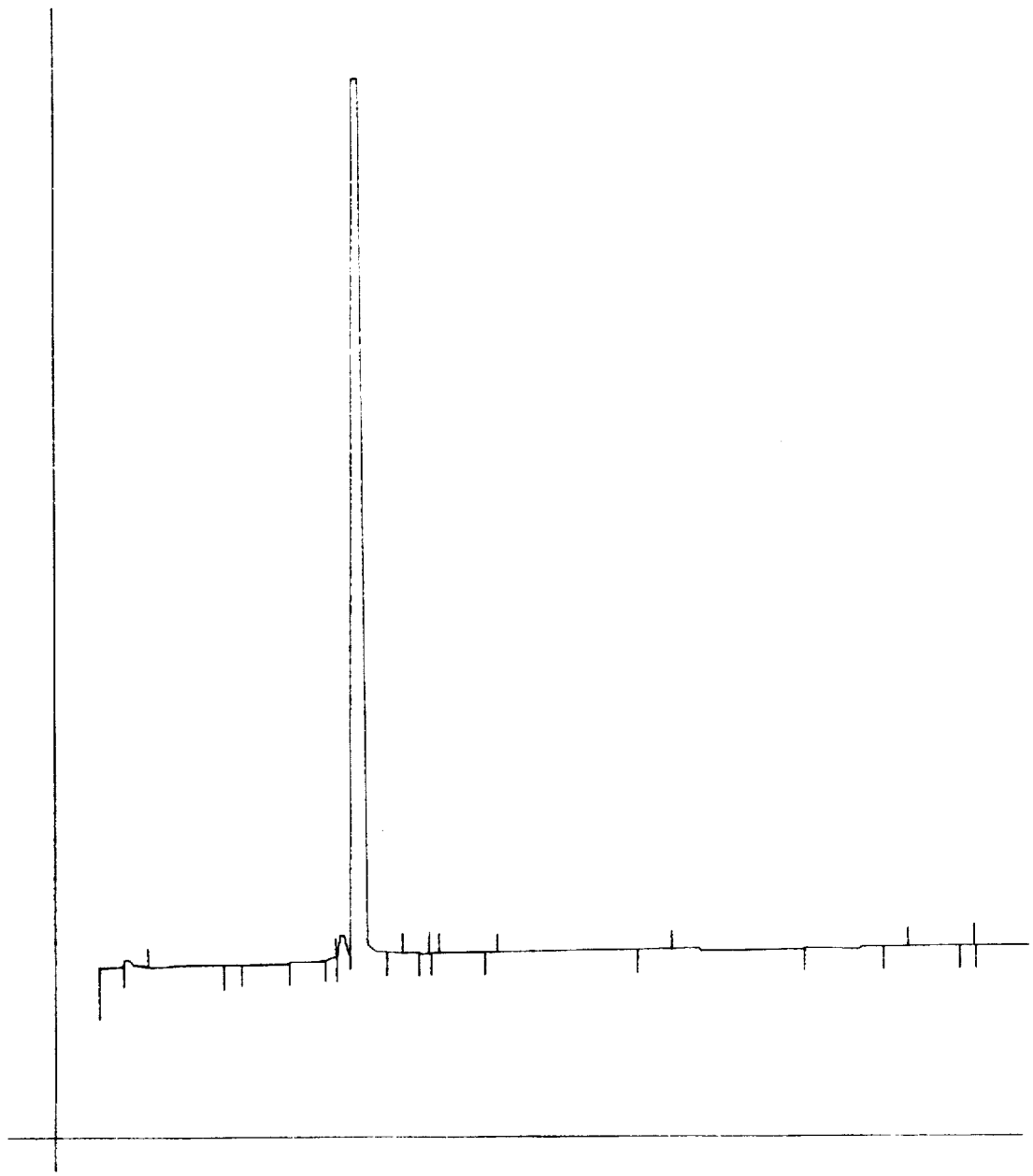

FIG. 11 is the GC spectrum for distillation Fraction 6 of the distillation product of the reaction product of Example III containing the compound having the structure:

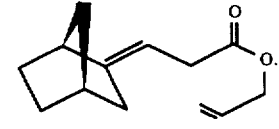

Figure 12:
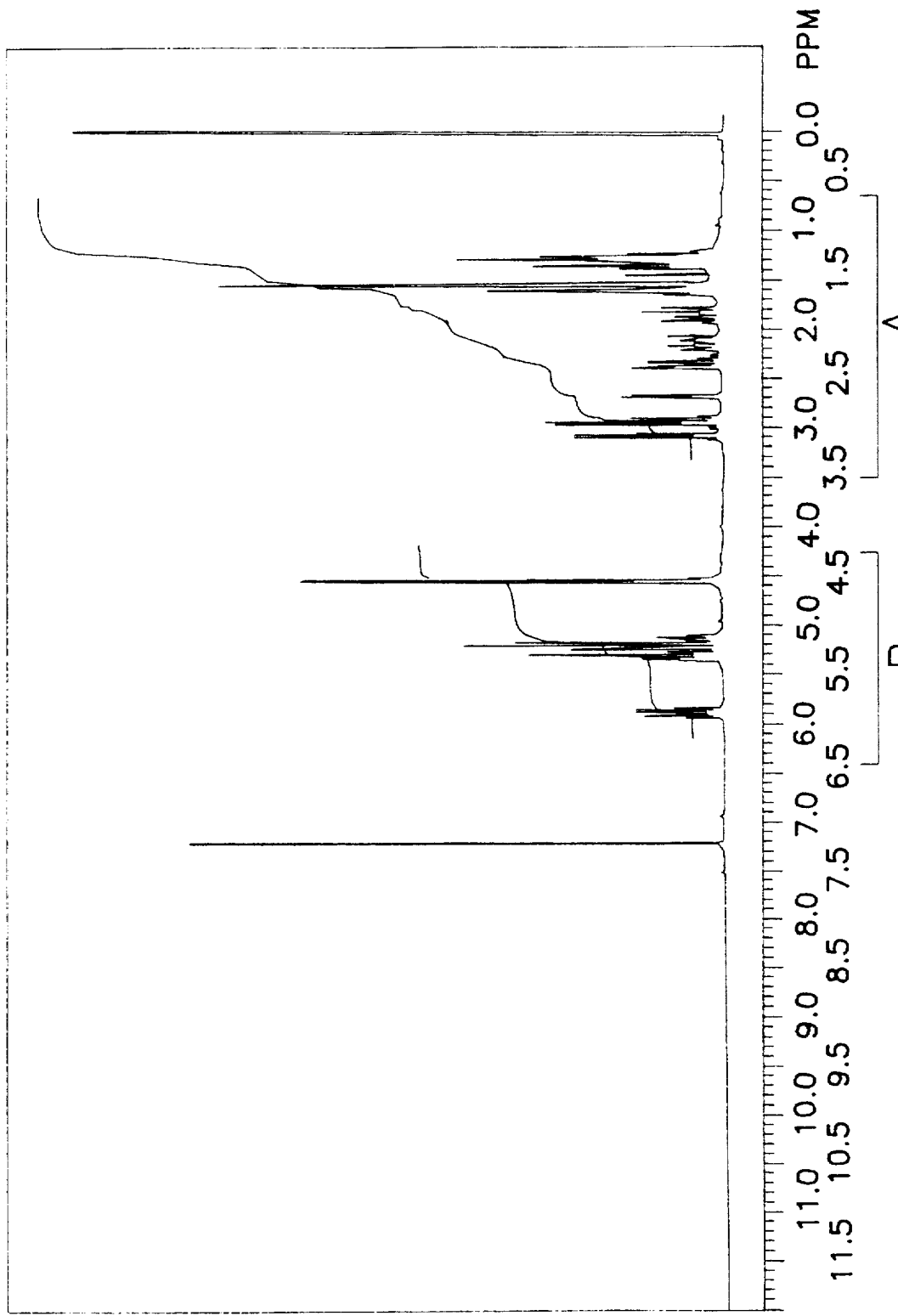

FIG. 12 is the NMR spectrum for the compound having the structure:

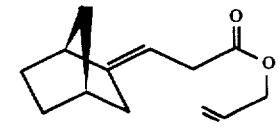

prepared according to Example III.

Figure 12A:
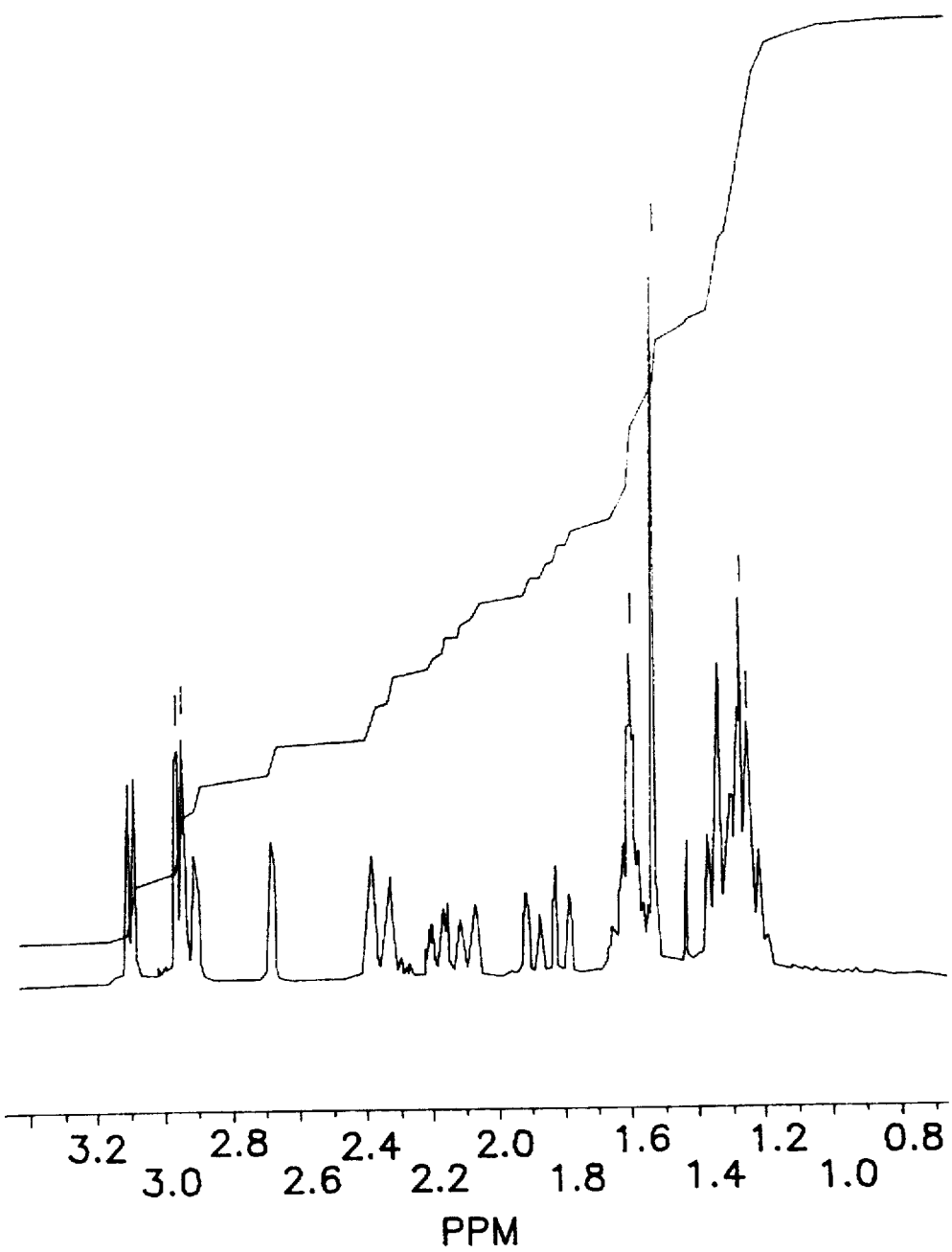

FIG. 12A is an enlargement of section "A" of the NMR spectrum of FIG. 12.

Figure 12B:
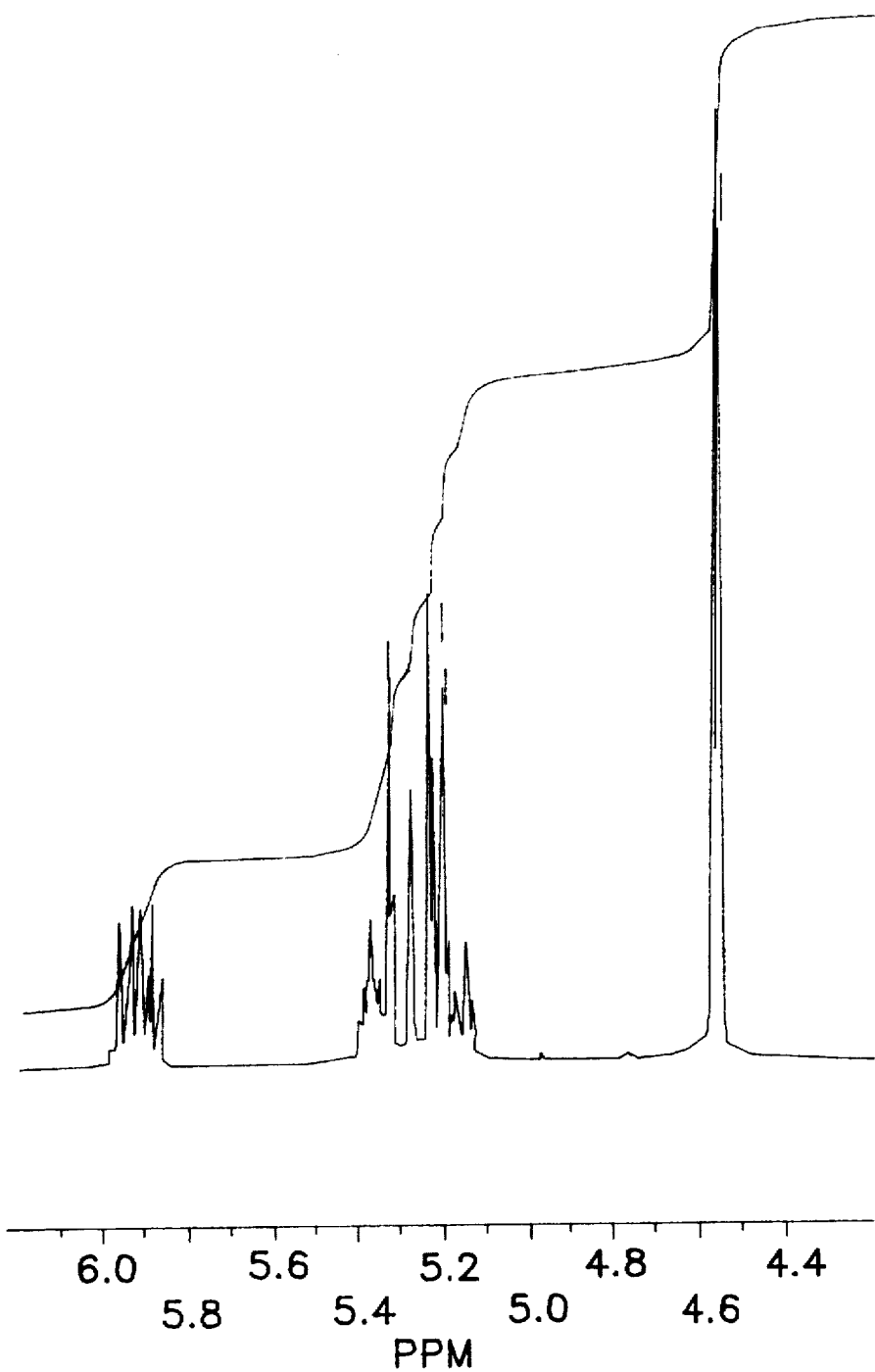

FIG. 12B is an enlargement of section "B" of the NMR spectrum of FIG. 12.

Figure 13:
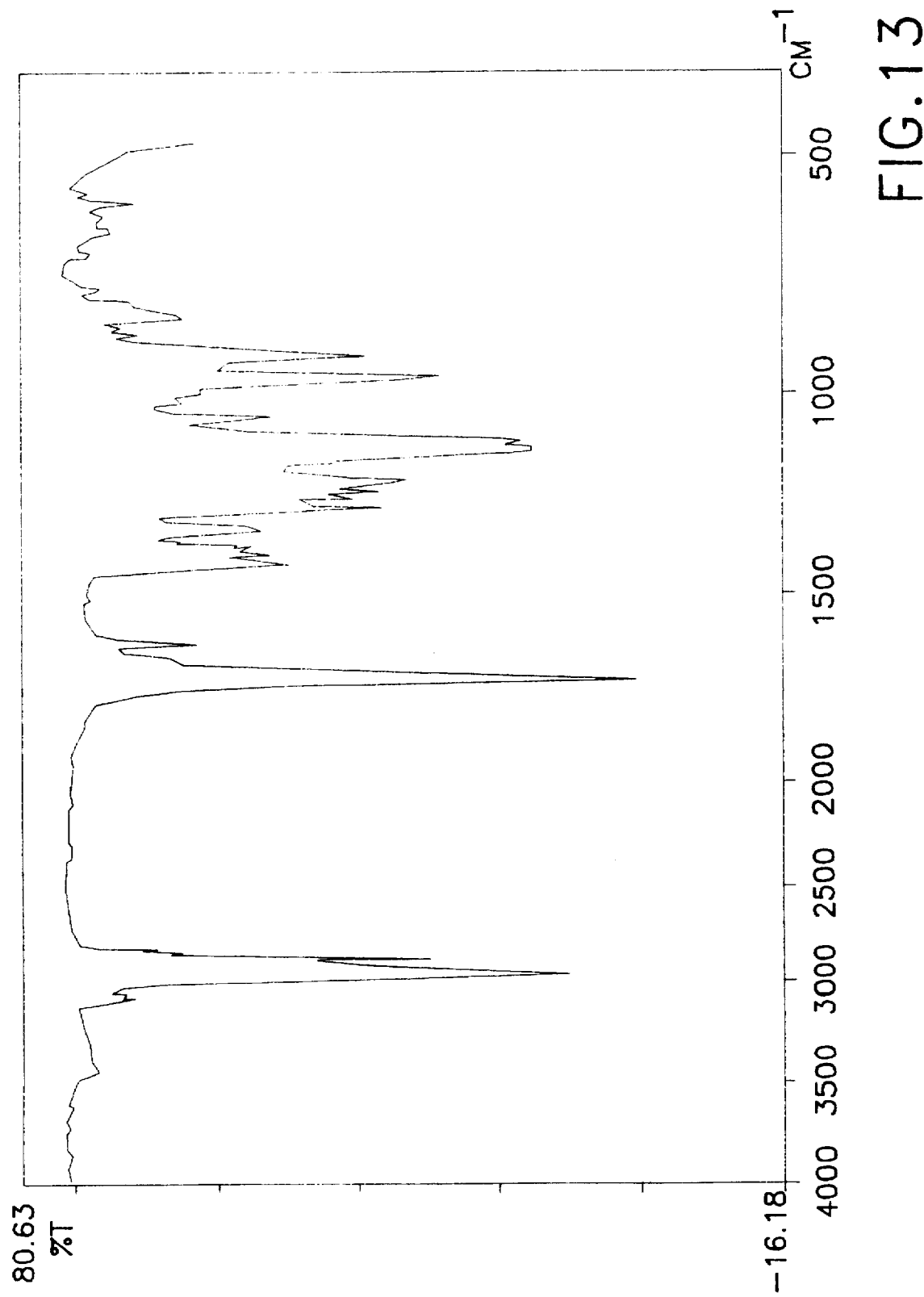

FIG. 13 is the infrared spectrum for the compound having the structure:

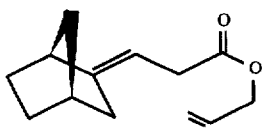

prepared according to Example III.

Figure 14:
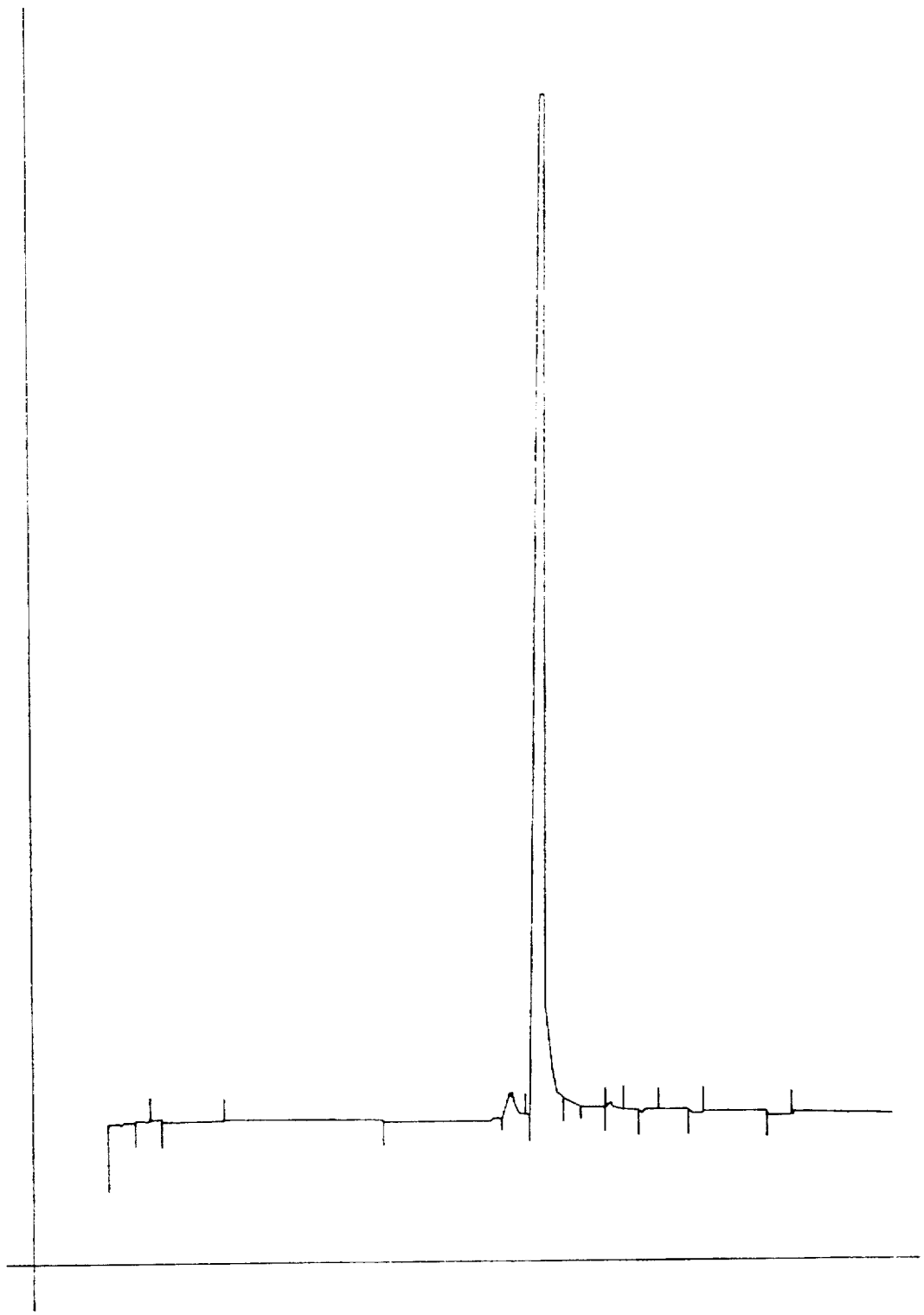

FIG. 14 is the GC spectrum for Fraction 7 of the distillation product of the reaction product of Example IV containing the compound having the structure:

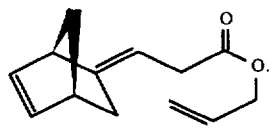

Figure 15:
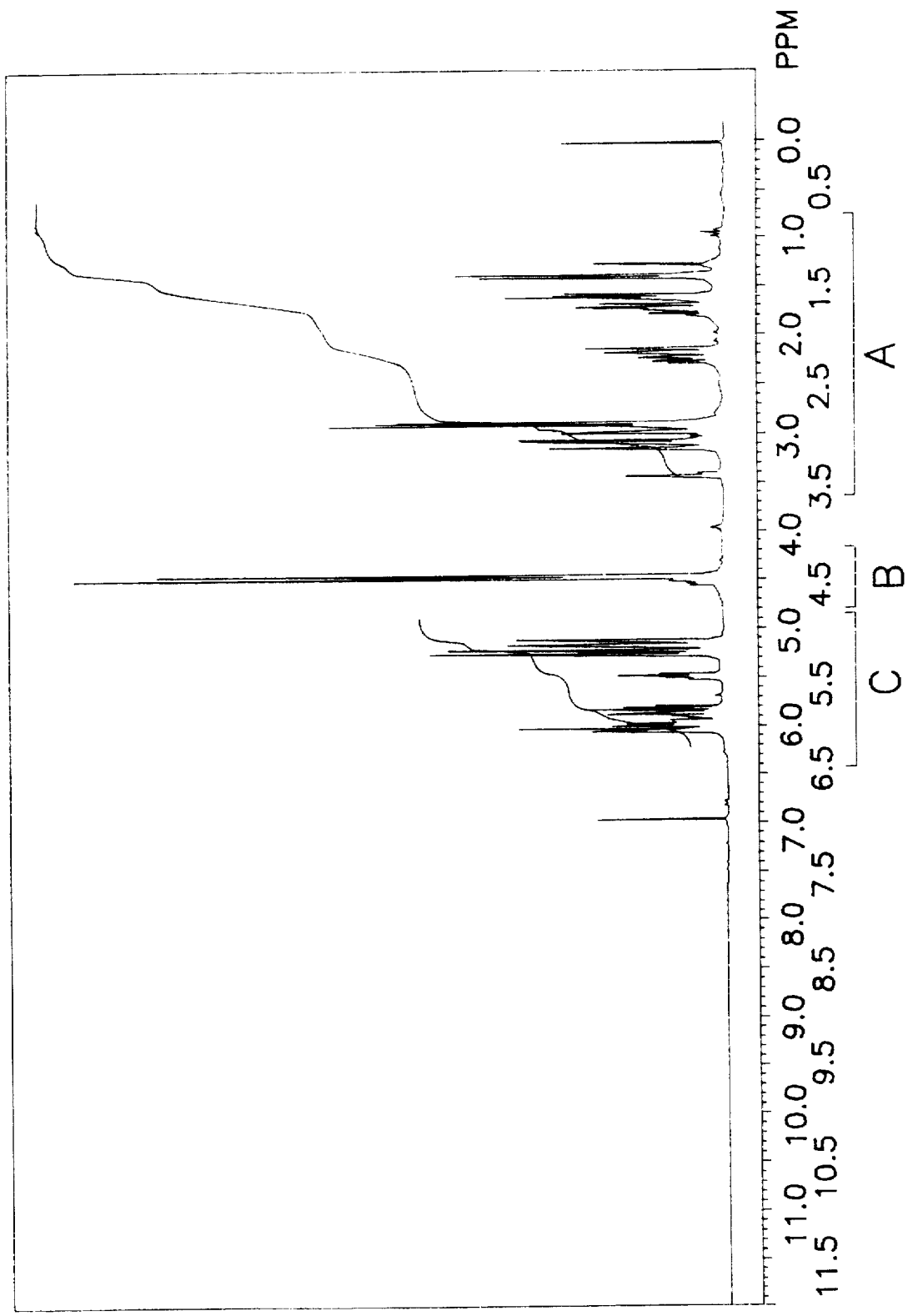

FIG. 15 is the NMR spectrum for the compound having the structure:

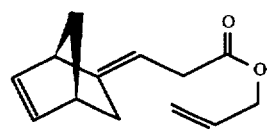

prepared according to Example IV.

Figure 15A:
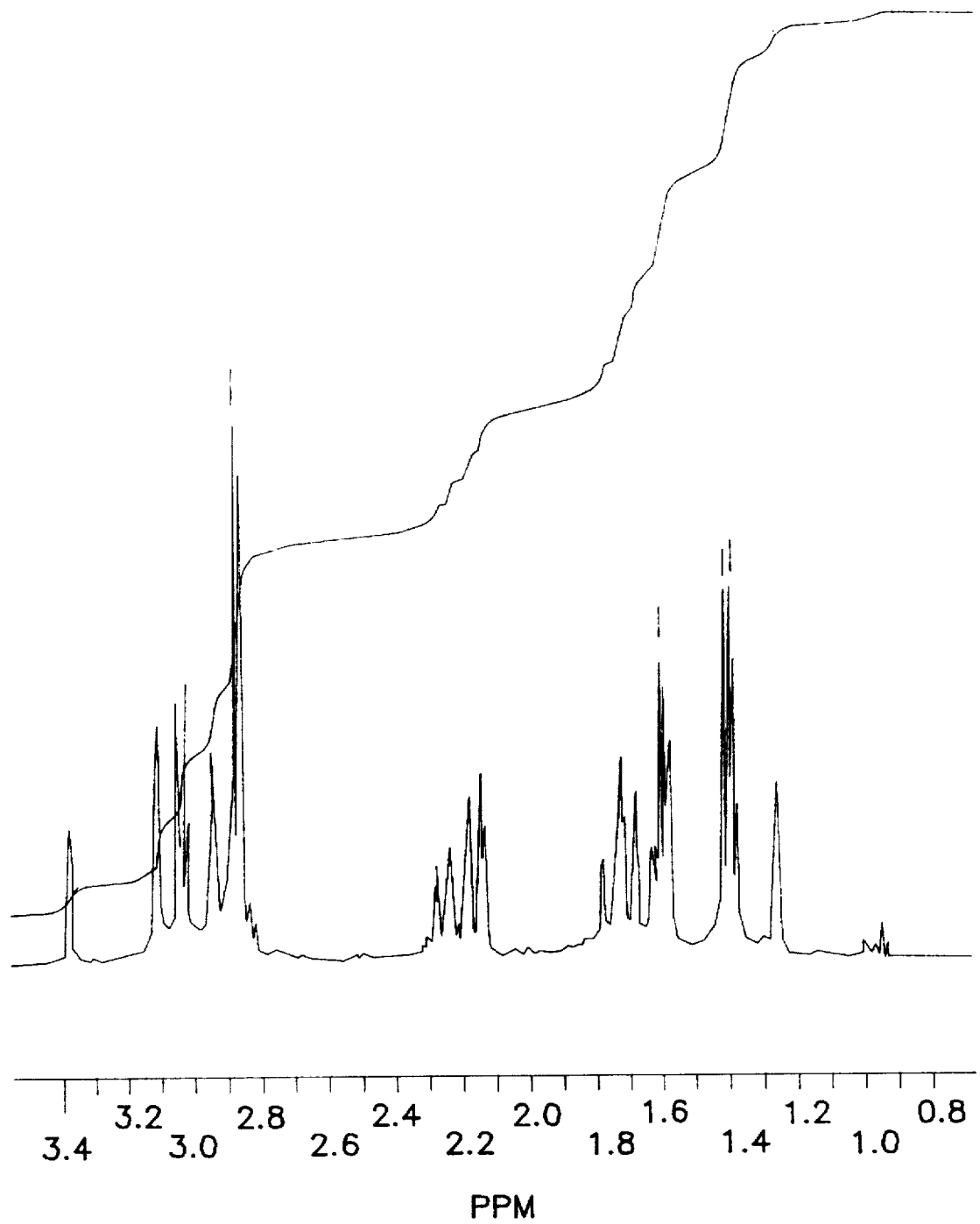

FIG. 15A is an enlargement of section "A" of the NMR spectrum of FIG. 15.

Figure 15B:
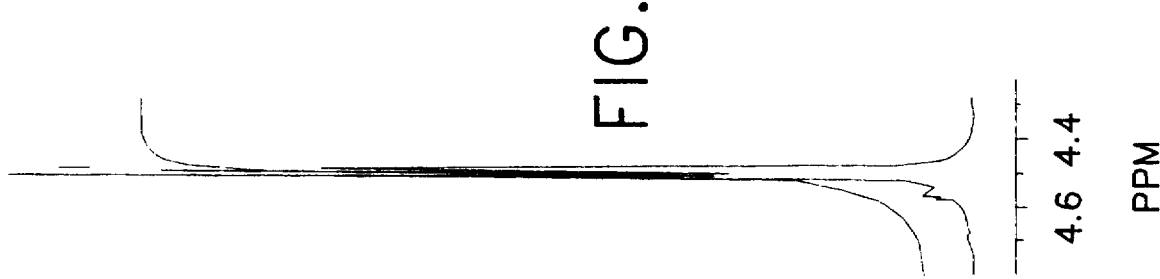

FIG. 15B is an enlargement of section "B" of the NMR spectrum of FIG. 15.

Figure 15C:
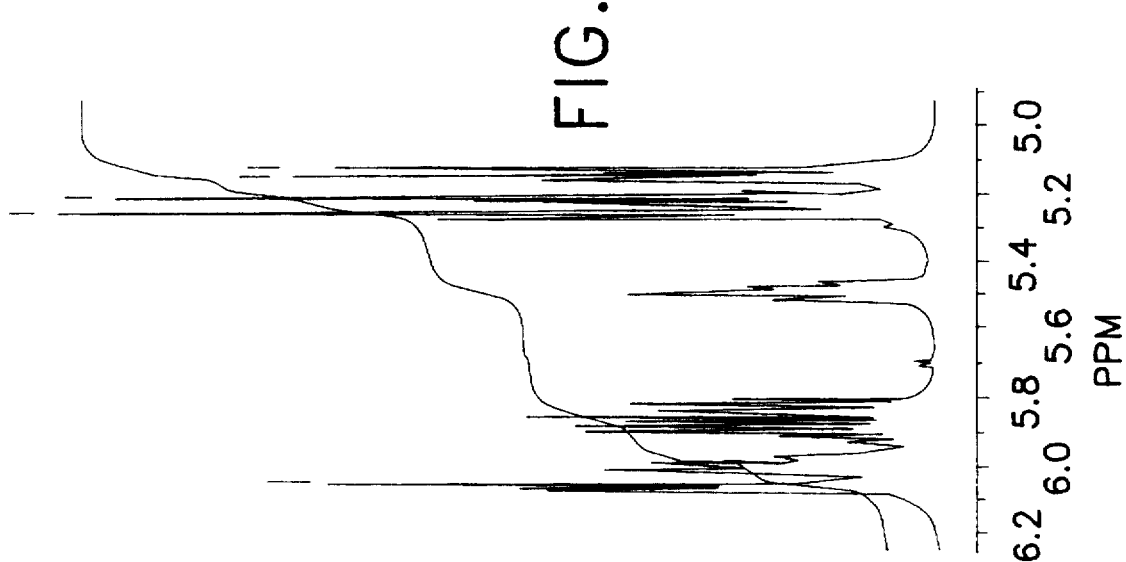

FIG. 15C is an enlargement of section "C" of the NMR spectrum of FIG. 15.

Figure 16:
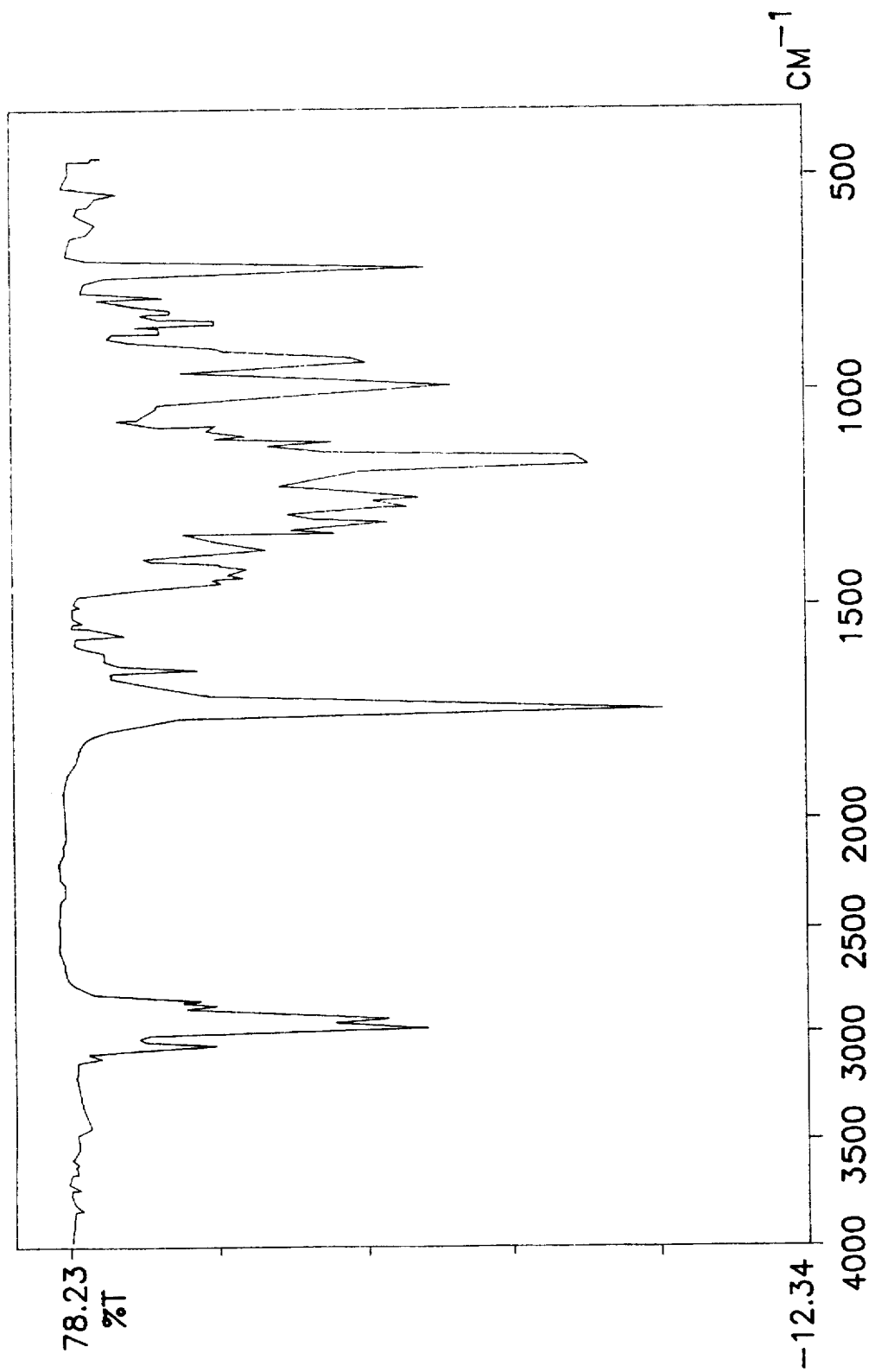

FIG. 16 is the infrared spectrum for the compound having the structure:

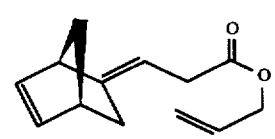

prepared according to Example IV.

Figures 17, 18:
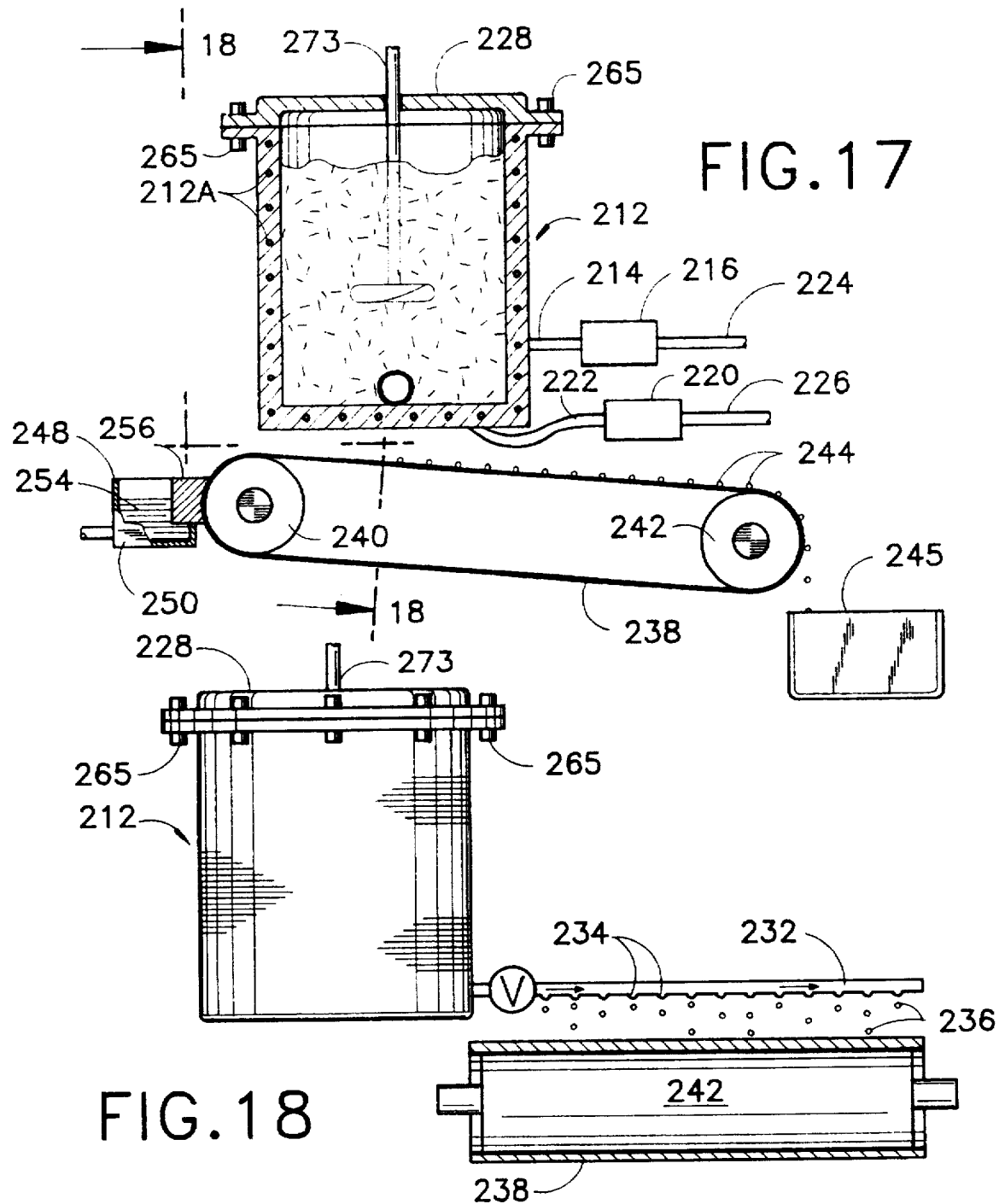

FIG. 17 represents a cutaway side elevation view of the apparatus used in forming perfumed polymers which contain imbedded in the interstices thereof at least one of the allyl esters of 2-norbornane acrylic acids and 2-norbornylidene propionic acids of our invention.

FIG. 18 is a front view of the apparatus of FIG. 17 looking in the direction of the arrows.

DETAILED DESCRIPTION OF THE DRAWINGS

Referring to the GC spectrum of FIG. 3, FIG. 3 is a GC spectrum of the reaction product of Example I(B). The peaks indicated by reference numeral 33 are the peaks for isomers of the compound having the structure:

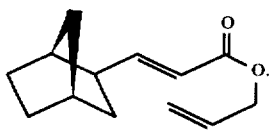

The peaks indicated by reference numeral 32 are for isomers defined according to the structure:

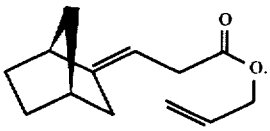

The peaks indicated by reference numeral 31 are the peaks for a lactone impurity defined according to the structure:

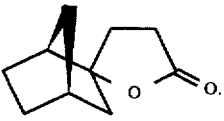

By the same token, the GC spectrum of FIG. 4 is also for the crude reaction product of Example I(B) run under different conditions. The peaks indicated by reference numeral 42 are the peaks for isomers of the desired compound having the structure:

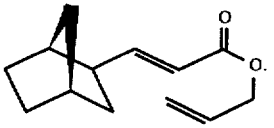

The peaks indicated by reference numeral 41 are for isomers of the compound defined according to the structure:

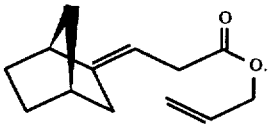

The peaks indicated by reference numeral 43 are for isomers defined according to the structure:

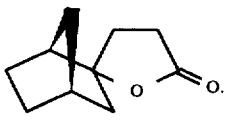

Referring to FIG. 10, the GC spectrum for the crude reaction product of Example III, the peak indicated by reference numeral 101 is the peak for the desired product having the structure:

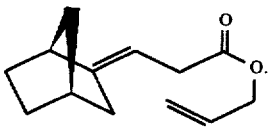

The peaks indicated by reference numeral 102 is for isomers defined according to the structure:

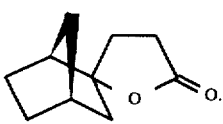

The peaks indicated by reference numeral 103 are for the carboxylic acids defined according to the structure:

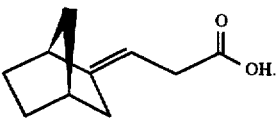

Referring to FIG. 11, the GC spectrum for distillation Fraction 6 of the distillation product of the reaction product of Example III, the peak indicated by reference numeral 110 is the peak for the compound having the structure:

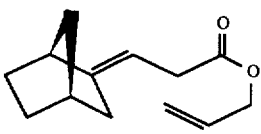

(conditions: carbowax column programmed from 80° to 220° C. at 8° C. per minute).

Referring to FIGS. 17 and 18, there is provided a process for forming scented polymer elements (wherein the polymer may be a thermoplastic polymer such as a low density polyethylene or polypropylene or copolymers of ethylene and vinyl acetate or mixtures of polymers and copolymers such as copolymers of ethylene and vinyl acetate and polyethylene) such as pellets useful in the formation of plastic particles useful in fabricating certain articles which may be perfumed. This process comprises heating the polymer or mixture of polymers to the melting point of said polymer or mixture of polymers, e.g., 250° C. in the case of low density polyethylene. The lower most portion of the container is maintained at a slightly lower temperature and the material in the container is taken off at such location for delivery through the conduit. Thus, referring to FIGS. 17 and 18, in particular, the apparatus used in producing such elements comprises a device for forming the polymer containing perfume, e.g., polyethylene or polyethylene-polyvinyl acetate or mixtures of same or polypropylene, which comprises a vat or container 212 into which the polymer taken alone or in admixture with other copolymers and the perfuming substance which is at least one of the allyl esters of 2-norbornane acrylic acids and 2-norbornylidene propionic acids of our invention and other compatible perfumes is placed. The container is closed by means of an air-tight lid 228 and clamped to the container by bolts 265. A stirrer 273 traverses the lid or cover 228 in an air-tight manner and is rotatable in a suitable manner. A surrounding cyclinder having heated coils 212A which are supplied with electric current through cable 214 from a rheostat or control 216 is operated to maintain the temperature inside the container 212 such that the polymer in the container will be maintained in the molten or liquid state. It has been found advantageous to employ polymers at such a temperature that the viscosity will be in the range of 90–100 Sayboldt seconds. The heater is operated to maintain the upper portion of the container 212 within a temperature range of, for example, 220°–270° C. in the case of low density polyethylene. The bottom portion of the container 212 is heated by means of heating coils 212A regulated through the control 220 connected thereto through a connecting wire 222 to maintain the lower portion of the container 212 within the temperature range of 220°–270° C.

Thus, the polymer or mixture of polymers added to the container 212 is heated from 10–12 hours, whereafter the perfume composition or perfume material which contains one or more of the allyl esters of 2-norbornane acrylic acids and 2-norbornylidene propionic acids of our invention is quickly added to the melt. Generally, about 10–45 percent by weight of the resulting mixture of the perfumery substance is added to the polymer.

After the perfume material is added to the container 212, the mixture is stirred for a few minutes, for example, 5–15 minutes and maintained within the temperature ranges indicated previously by the heating coils 212A. The controls 216 and 220 are connected through cables 224 and 226 to a suitable supply of electric current for supplying the power for heating purposes.

Thereafter, the valve "V" is opened permitting the mass to flow outwardly through conduit 232 having a multiplicity of orifices 234 adjacent to the lower side thereof. The outer end of the conduit 232 is closed so that the liquid polymer in intimate admixture with one or more of the allyl esters of 2-norbornane acrylic acids and 2-norbornylidene propionic acids of our invention or mixture of perfume substances and one or more of the allyl esters of 2-norbornane acrylic acids and 2-norbornylidene propionic acids of our invention will continuously drop through the orifices 234 downwardly from the conduit 232. During this time, the temperature of the polymer intimately admixed with the perfumery substance in the container 212 is accurately controlled so that a temperature in the range of from about 240°–250° C., for example (in the case of low density polyethylene), will exist in the conduit 232. The regulation of the temperature through the controls 216 and 220 is essential in order to insure temperature balance to provide for the continuous dripping or dropping of molten polymer intimately admixed with the perfume substance which is all of or which contains at least one of the allyl esters of 2-norbornane acrylic acids and 2-norbornylidene propionic acids of our invention, through the orifices 234 at a rate which will insure the formation of droplets 236 which will fall downwardly onto a moving conveyor belt 238 caused to run between conveyor wheels 240 and 242 beneath the conduit 232.

When the droplets 236 fall onto the conveyor belt 238, they form pellets which harden almost instantaneously and fall off the end of the conveyor belt 238 into a container 245 which is advantageously filled with water or some other suitable cooling liquid to insure the rapid cooling of each of the pellets. The pellets are then collected from the container 245 and utilized for the formation of other functional products, e.g., garbage bags and the like. The conveyor belt 238 is cooled by cooling water 254 contained in container 250 having sidewalls 248. The cooling water is absorbed in sponge 256 which cools the conveyor belt 238 as wheels 240 and 242 are moving.

THE INVENTION

The present invention provides allyl esters of 2-norbornane acrylic acids and 2-norbornylidene propionic acids defined according to the generic structure:

wherein the wavy line represents a carbon-carbon single bond or a carbon-carbon double bond; wherein one of the dashed lines is a carbon-carbon single bond and the other of the dashed lines is a carbon-carbon double bond; and wherein R represents methyl or hydrogen. Preferably, the allyl esters of 2-norbornane acrylic acids and 2-norbornylidene propionic acids of our invention are compounds having the structures:

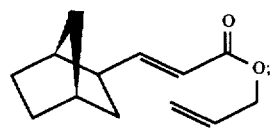

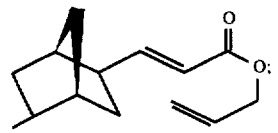

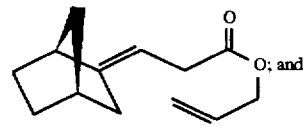

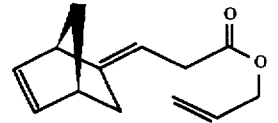

which include each of the geometric and optical isomers of the compounds.

The present invention also provides processes for preparing such allyl esters of 2-norbornane acrylic acids and 2-norbornylidene propionic acids by means of carrying out the reaction sequence:

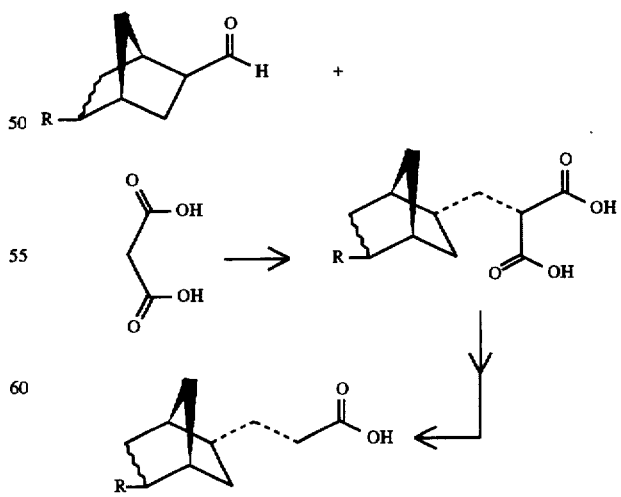

and then either reacting the resultant reaction product with allyl alcohol according to the reaction:

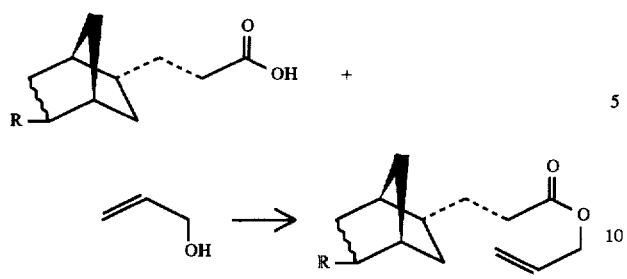

or first reacting the resulting product with an esterification reagent according to the reaction:

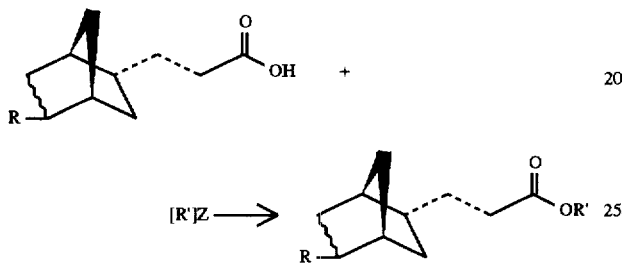

wherein the compound, to wit: [R'] —Z— is an esterification reagent wherein R' represents $C_1$–$C_5$ alkyl and Z represents hydroxyl, iodide or sulfate. In the latter case, the resulting alkyl ester is then reacted with allyl alcohol according to the reaction:

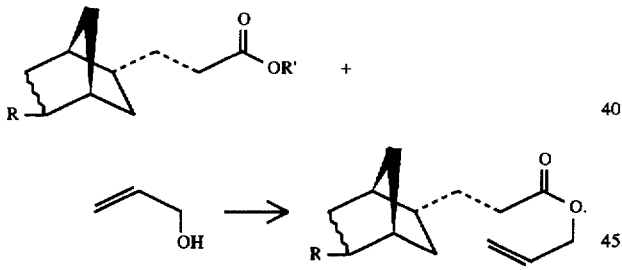

When it is desired to make compounds such as those having the structure:

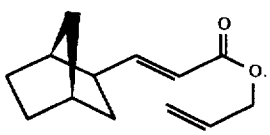

the reaction:

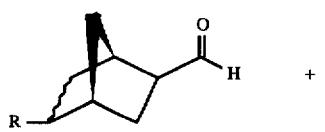

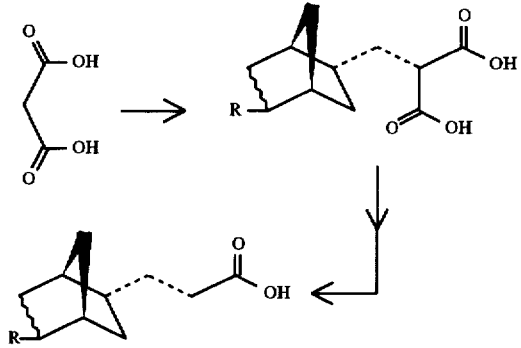

is carried out in the presence of a mixed pyridine and piperidine catalyst at a temperature of 90° C. At the end of the reaction forming the dicarboxylic acid, the reaction mass pH is raised using a strong base (such as 50% sodium hydroxide solution) to a range of between 11 and 11.5. In order to decarboxylate the resulting product, the reaction mass is acidified and heated whereby the pH is reduced to about 1 using, for example, hydrochloric acid.

When it is desired to produce compounds such as those having the structures:

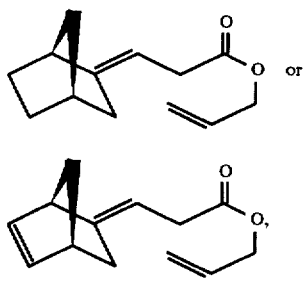

a trialkyl amine catalyst is used for the reaction:

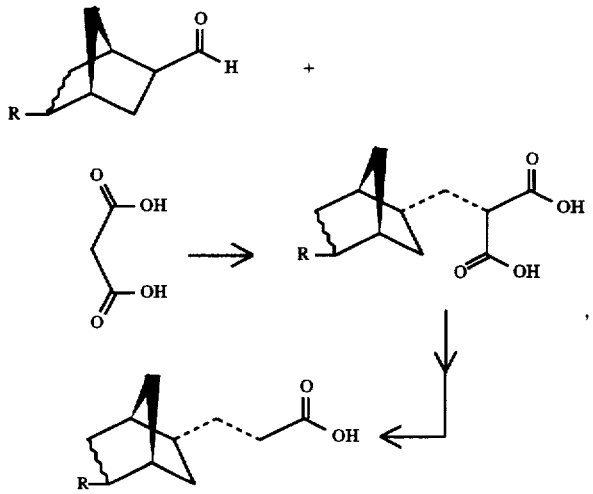

which trialkyl amine is defined according to the structure:

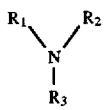

wherein $R_1$, $R_2$ and $R_3$ are the same or different $C_1$–$C_3$ alkyl, preferably methyl or ethyl. The reaction temperature for the reaction:

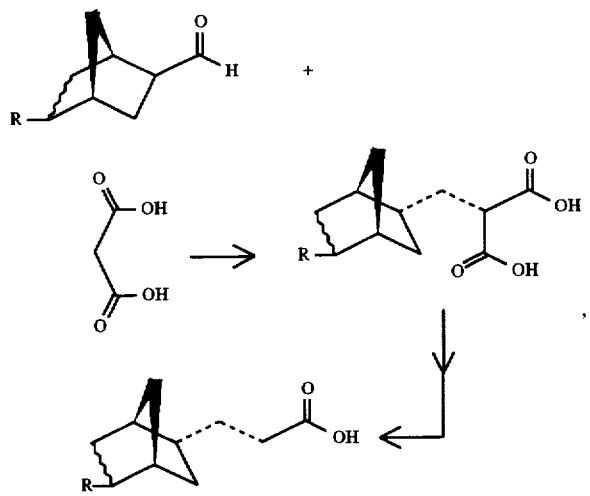

is still at about 90° C. The pH of the reaction mass is raised at the end of the reaction to approximately 12 and is then lowered to approximately 1.5 with strong acid.

The reaction:

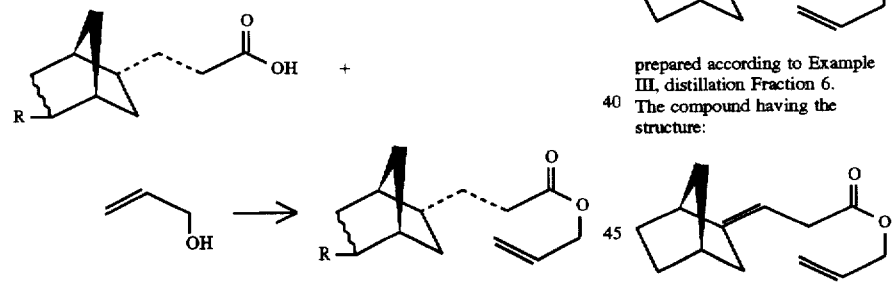

is carried out in the presence of an acid catalyst such as methane sulfonic acid or an acid ion exchange resin catalyst a such as AMBERLYST® 15. The reaction is carried out at reflux conditions, preferably at atmospheric pressure at a temperature in the range of from about 150° up to about 170° C. for a period of time of from about 10 up to about 15 hours.

At the end of the reaction, the reaction mass is "worked up" by means of extraction followed by fractional distillation using standard fractional distillation techniques.

Thus, the allyl esters of 2-norbornane acrylic acids and 2-norbornylidene propionic acids of our invention augment, enhance or impart coconut, pineapple-like, fruity, lactonic, coumarin-like, sweet, animalic and sweaty aromas with floral undertones and pineapple, coconut, galbanum, sweet, herbaceous, oolong tea-like, sweaty and animalic topnotes in or to perfume compositions, colognes and perfumed articles (including soaps, anionic, cationic, nonionic or zwitterionic detergents, fabric softener compositions, fabric softener articles, optical brightener compositions, perfumed polymers, hair preparations and the like, thus fulfilling a need in the field of perfumery as well as detergent, cologne, fabric softener and cosmetic manufacture.

Examples of the allyl esters of 2-norbornane acrylic acids and 2-norbornylidene propionic acids of our invention which are useful in the practice of our invention and their perfumery properties are set forth in the following Table I.

TABLE I

| Structure of Compound | Perfumery Evaluation |
|---|---|
| The compound having the structure: <br><br> prepared according to Example I(B) bulked distillation Fractions 7–20. | A coconut, pineapple-like, fruity, lactonic aroma with pineapple and galbanum topnotes and floral undertones |
| The compound having the structure: <br><br> prepared according to Example II. | A coumarin-like, lactonic aroma, with sweet, herbaceous and oolong tea-like topnotes. |
| The compound having the structure: <br><br> prepared according to Example III, distillation Fraction 6. | A sweaty, animalic, fruity and pineapple aroma with galbanum, sweaty and animalic topnotes. |
| The compound having the structure: <br><br> prepared according to Example IV, bulked distillation Fractions 5–10. | A sweaty, animalic aroma with coconut, sweaty, and animalic topnotes. |

One or more of the of the allyl esters of 2-norbornane acrylic acids and 2-norbornylidene propionic acids of our invention prepared in accordance with the process of our invention and one or more auxiliary perfume ingredients including, for example, alcohols, aldehydes, ketones, terpenic hydrocarbons, nitriles, esters other than the esters of our invention, lactones, natural essential oils and synthetic essential oils may be admixed so that the combined odors of the individual components produce a pleasant and desired fragrance particularly and preferably in the floral and galbanum area of fragrances. Such perfume compositions usually contain (a) the main note or the "bouquet" or foundation stone of the composition; (b) modifiers which round off and accompany the main note; (c) fixatives which include odorous substances which lend a particular note to the perfume throughout all stages of evaporation and substances which retard evaporation; and (d) topnotes which are usually low boiling, fresh smelling materials.

In perfume compositions, it is the individual components which contribute to their particular olfactory characteristics, however, the overall sensory effect of the perfume composition will be at least the sum total of the effects of each of the ingredients. Thus, one or more of the allyl esters of 2-norbornane acrylic acids and 2-norbornylidene propionic acids of our invention prepared in accordance with the processes of our invention can be used to alter, modify, impart or enhance the aroma characteristics of a perfume composition, for example, by utilizing or moderating the olfactory reaction contributed by another ingredient in the composition.

The amount of one or more of the allyl esters of 2-norbornane acrylic acids and 2-norbornylidene propionic acids of our invention prepared in accordance with the processes of our invention which will be effective in perfume compositions as well as in perfumed articles (e.g., anionic, nonionic, cationic and zwitterionic solid or liquid detergents, soaps, fabric softener compositions, drier-added fabric softener articles, optical brightener compositions, perfumed polymers and textile sizing agents) and colognes depends on many factors including the other ingredients, their amounts and the effects which are desired. It has been found that perfume compositions containing as little as 0.01% of one or more of the allyl esters of 2-norbornane acrylic acids and 2-norbornylidene propionic acids of our invention prepared in accordance with the processes of our invention and even up to 100% of one or more of the allyl esters of 2-norbornane acrylic acids and 2-norbornylidene propionic acids of our invention or even less(e.g., 0.005%) can be used to impart, augment or enhance coconut, pineapple-like, fruity, lactonic, coumarin-like, sweet, animalic and sweaty aromas with floral undertones and pineapple, coconut, galbanum, sweet, herbaceous, oolong tea-like, sweaty and animalic topnotes in or to soaps, cosmetics, solid or liquid anionic, nonionic, cationic and zwitterionic detergents, fabric softener compositions, fabric softener articles, optical brightener compositions, textile sizing compositions, perfumed polymers or other products. The amount employed can range up to 100% of the fragrance components and will depend on considerations of cost, nature of the end product, the effect desired on the finished product and the particular fragrance sought.

One or more allyl esters of 2-norbornane acrylic acids and 2-norbornylidene propionic acids prepared in accordance with the processes of our invention are useful (taken alone or together with other ingredients in perfume compositions) as (an) olfactory component(s) in detergents and soaps, space odorants and deodorants, perfumes, colognes, toilet water, bath preparations, such as creams, deodorants, hand lotions and sun screens; powders such as talcs, dusting powders, face powders, and perfumed polymers and articles of manufacture produced from said perfumed polymers, e.g., garbage bags, children's toys and the like. When used as (an) olfactory component(s) as little as 0.2% of one or more of the allyl esters of 2-norbornane acrylic acids and 2-norbornylidene propionic acids of our invention prepared in accordance with the processes of our invention will suffice to impart, augment or enhance intense and substantive coconut, pineapple-like, fruity, lactonic, coumarin-like, sweet, animalic and sweaty aromas with floral undertones and pineapple, coconut, galbanum, sweet, herbaceous, oolong tea-like, sweaty and animalic topnotes to floral and galbanum fragrance formulations. Generally, no more than 6% of one or more of the allyl esters of 2-norbornane acrylic acids and 2-norbornylidene propionic acids of our invention based on the ultimate end product as required in the perfumed article composition is required. Accordingly, the range of allyl esters of 2-norbornane acrylic acids and 2-norbornylidene propionic acids in the perfumed article is from about 0.2% by weight of the allyl esters of 2-norbornane acrylic acids and 2-norbornylidene propionic acids up to about 6% by weight of the allyl esters of 2-norbornane acrylic acids and 2-norbornylidene propionic acids based on the total weight of the perfumed article.

In addition, the perfume composition or fragrance composition of our invention can contain a vehicle or carrier for one or more of the allyl esters of 2-norbornane acrylic acids and 2-norbornylidene propionic acids of our invention prepared in accordance with the processes of our invention. The vehicle can be a liquid such as a non-toxic alcohol, e.g., ethyl alcohol, a non-toxic glycol, e.g., propylene glycol or the like. The carrier can also be an absorbent solid such as gum (e.g., gum arabic or xanthan gum) or components for encapsulating the compositions (such as gelatin as by coacervation) or such as a urea formaldehyde prepolymer forming a capsule shell around a liquid perfumed center.

Our invention also relates to the utilization of controlled released technology for the controlled release of perfumes into gaseous environments from polymers such as mixtures of epsilon polycaprolactone polymers and polyethylene which polyepsilon caprolactone polymers are defined as set forth at columns 29–30 of U.S. Pat. No. 4,521,634 issued on Jun. 4, 1985, the specification for which is incorporated by reference herein.

The following Examples I–IV serve to illustrate processes for preparing the allyl esters of 2-norbornane acrylic acids and 2-norbornylidene propionic acids of our invention. The examples following Example IV are illustrative of the organoleptic utilities of the allyl esters of 2-norbornane acrylic acids and 2-norbornylidene propionic acids of our invention. All parts and percentages given herein are by weight unless otherwise specified.

EXAMPLE I

Preparation of the Allyl Ester of 2-Norbornane Acrylic Acid

Example I(A): Preparation from the Methyl Ester of 2-Norbornane Acrylic Acid

Reaction:

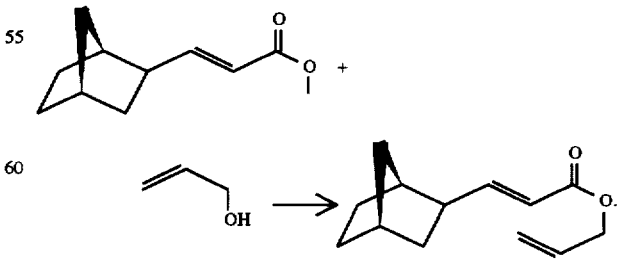

54 Grams of methyl-2-norbornane acrylate having the structure:

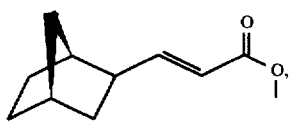

32 grams of allyl alcohol, 75 grams of cumene and 1.5 grams of sodium carbonate were charged to a 250 ml distillation flask equipped with heating mantle, thermometer and reflux condenser. The reaction mass is refluxed for a period of 2 hours at approximately 165° C.

Figure 1:
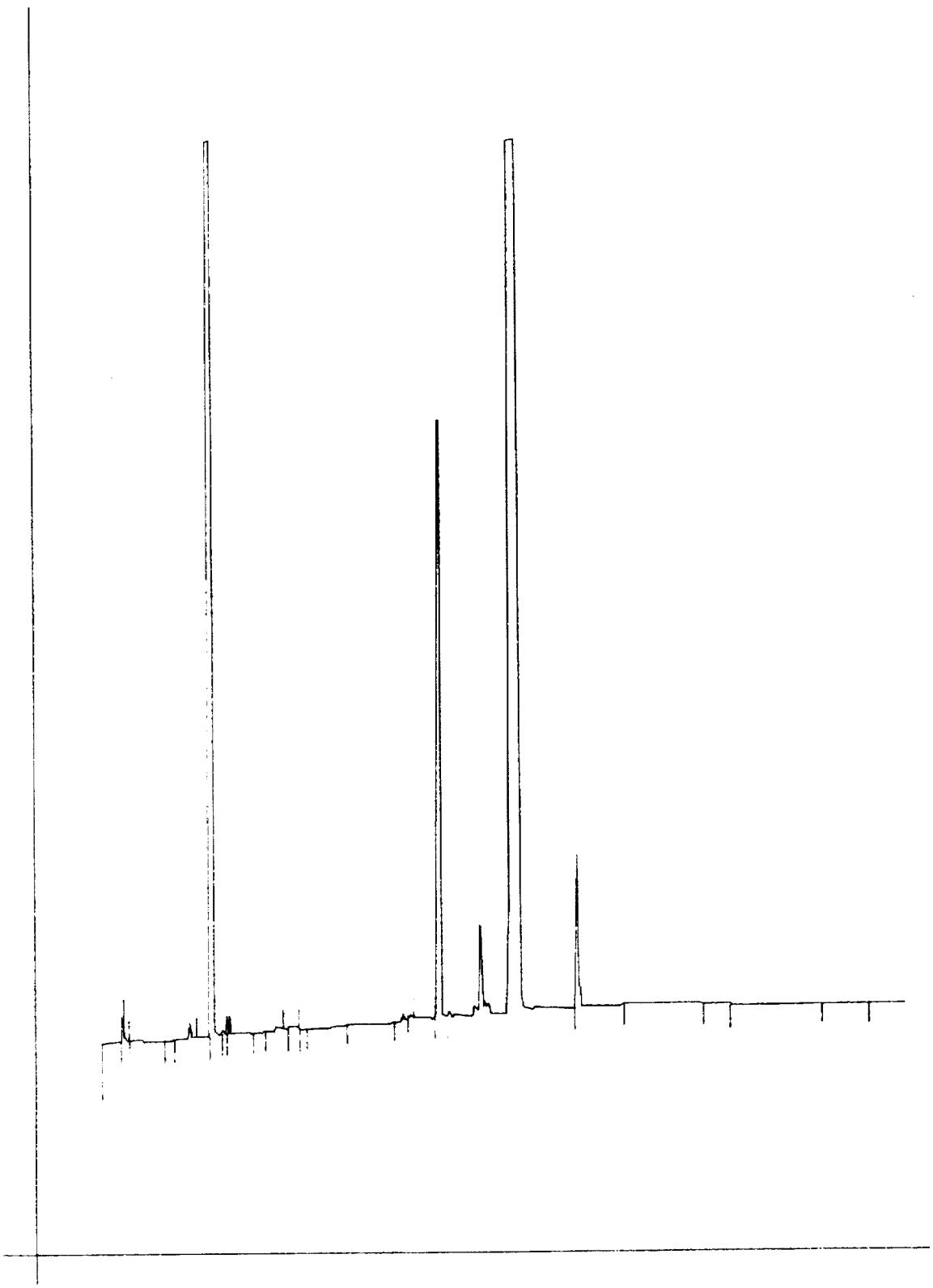
FIG. 1 is the GC spectrum for the crude reaction product of Example I(A) containing the compound having the structure.

The reaction mass is then washed with two 200 ml portions of water. The resulting product having the structure:

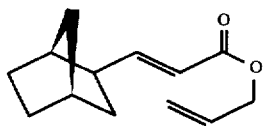

was then trapped out for odor using a ten foot×half inch 10% SE-30 stainless steel column programmed from 75°–220° C. at 50° C. per minute. The GC spectrum for the compound having the structure:

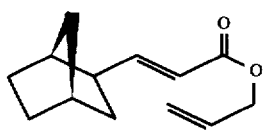

prepared in this manner is set forth in FIG. 1.

Example I(B): Product Prepared Using 2-Norbornane Acrylic Acid Reactant

Reactions:

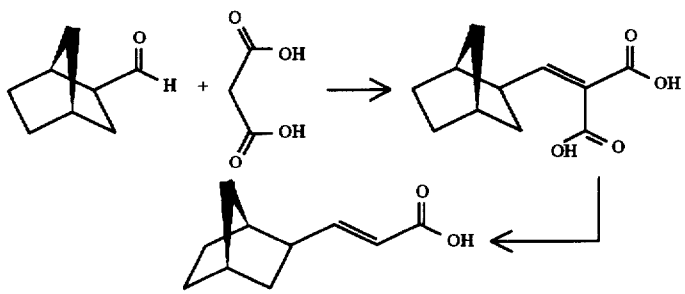

and

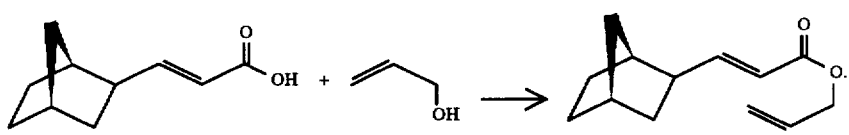

Into a 5 liter reaction flask equipped with stirrer, thermometer, reflux condenser and heating mantle are placed 875 grams of norbornane carboxaldehyde having the structure:

930 grams of malonic acid having the structure:

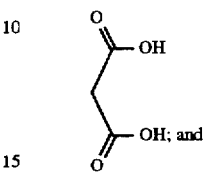

1,000 grams of pyridine and 5.0 grams of piperidine. With stirring, the reaction mass is heated to 90° C. and maintained at 90° C. for a period of 10.5 hours. The reaction mass is then slowly cooled to a temperature of between 30° and 35° C. and 343.2 grams of 50% sodium hydroxide (aqueous) is added to the reaction mass bringing the reaction mass pH to 11.2.

The pyridine was stripped off at 32 mm/Hg. pressure at 50° C., removing 934 grams of pyridine.

1,300 Grams of hydrochloric acid (concentrated) was added to the reaction mass bringing the reaction mass pH to approximately 0.09.

The 1,300 grams of hydrochloric acid caused dissolution of all solids in the reaction mass.

The reaction mass exists now in two phases: an aqueous phase and an organic phase. The aqueous phase was extracted with 200 grams of toluene three times. The toluene layer and the toluene extracts were again washed with three 200 gram portions of 10% aqueous hydrochloric acid. The toluene layer is then returned to the 5 liter reaction vessel and 400 grams of allyl alcohol and 7.5 grams of methane sulfonic acid is added using a Bidwell trap. The reaction mass is refluxed for a period of 11 hours removing water using the Bidwell trap. An additional 100 grams of allyl alcohol is then added and the reaction mass is refluxed for a period of 7 hours. Then another 100 grams of allyl alcohol is added and the reaction mass is refluxed for an additional 7 hours.

7.5 Grams of sodium acetate is added to the reaction mass and the reaction mass is stirred for a period of 30 minutes. The allyl alcohol (excess) is then stripped off and the resulting product is washed with two 200 grams of water bringing the pH of the reaction product to 5.

167.5 Grams of crude reaction mass is recovered containing the compound having the structure:

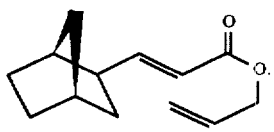

The resulting product is first rushed over on a 12 inch Vigreux column and then fractionally distilled through an 8 inch Goodloe packed column yielding the following fractions:

| Fraction Number | Vapor Temperature (°C.) | Liquid Temperature (°C.) | Vacuum mm/Hg. Pressure | Weight of Fraction |
|---|---|---|---|---|
| 1 | 79/83 | 23/119 | 1.7/1.1 | 11.6 |
| 2 | 91 | 122 | 1.6 | 10.8 |
| 3 | 93 | 123 | 1.6 | 20.6 |
| 4 | 93 | 122 | 1.6 | 20.0 |
| 5 | 94 | 122 | 1.6 | 23.2 |
| 6 | 93 | 122 | 1.5 | 42.6 |
| 7 | 93 | 123 | 1.5 | 57.8 |
| 8 | 93 | 123 | 1.5 | 39.8 |
| 9 | 93 | 122 | 1.5 | 43.2 |
| 10 | 94 | 125 | 1.5 | 41.3 |
| 11 | 94 | 127 | 1.5 | 57.2 |
| 12 | 95 | 128 | 1.5 | 46.2 |
| 13 | 95 | 128 | 1.5 | 55.1 |
| 14 | 105 | 130 | 1.8 | 43.7 |
| 15 | 101 | 130 | 2.0 | 93.4 |
| 16 | 54/96 | 120/128 | 1.5 | 27.4 |
| 17 | 95 | 127 | 1.5 | 49.5 |
| 18 | 95 | 127 | 1.5 | 51.2 |
| 19 | 95 | 125 | 1.4 | 88.9 |
| 20 | 96 | 126 | 1.4 | 115.6 |
| 21 | 96 | 127 | 1.4 | 82.3 |
| 22 | 96 | 126 | 1.4 | 87.8 |
| 23 | 96 | 134 | 1.5 | 39.6 |
| 24 | 78 | 160 | 1.6 | 20.6 |
| 25 | 39 | 185 | 1.6 | 6.9 |

Fractions 7–20 are bulked. Bulked distillation Fractions 7–20 have GC spectra as set forth in FIGS. 3 and 4.

The conditions for the GC spectrum for FIG. 3 are: 50 meter×0.32 mm bonded fused silica column coated with methyl silicone programmed from 75°–225° C. at 2° C. per minute.

The conditions for the GC spectrum for FIG. 4 are: carbowax 20M coated on non-bonded fused silica, the column having measurements of 50 meters×0.32 mm programmed from 75°–225° C. at 2.0° C. per minute.

EXAMPLE II

Preparation of 2-(5-Methylbnorbornyl) Acrylic Acid, Allyl Ester

Reaction:

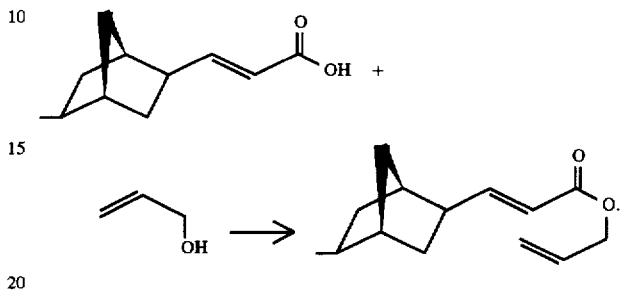

Into a 100 cc reaction vessel equipped with stirrer, thermometer and reflux condenser are placed 10 grams of the compound having the structure:

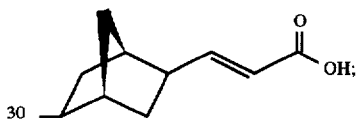

20 grams of allyl alcohol; and 2.0 grams AMBERLYST® 15 acid ion exchange catalyst.

The reaction mass is heated to reflux at 95°–96° C. and maintained at 95°–96° C. with stirring during reflux for a period of 17 hours. The resulting product is trapped on a GC apparatus (gas chromatograph apparatus) with the GC column being programmed from 80°–220° C. at 8° C. per minute (SE megabor column). The GC spectrum is set forth in FIG. 7.

The above reaction is repeated on a large scale yielding the compound having the structure:

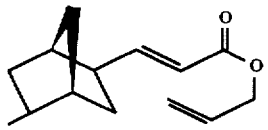

in a large enough quantity to prepare a fragrance formulation as set forth in Example V, infra.

EXAMPLE III
Preparation of the Allyl Ester of 2-Norbornylidene Acrylic Acid

Reactions:

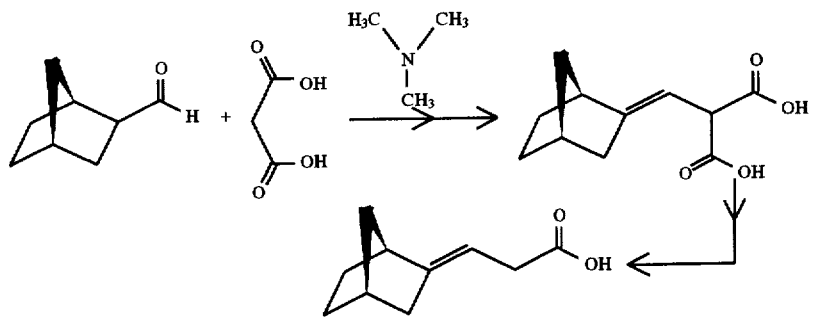

and

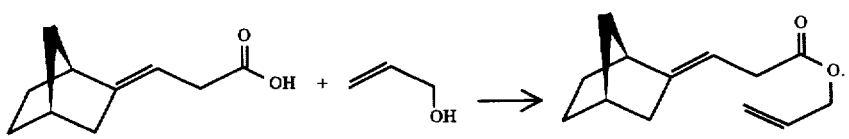

Into a 2 liter reaction flask equipped with stirrer, thermometer and reflux condenser are placed 275 grams of 5-norbornane-2-carboxaldehyde having the structure:

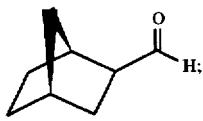

312 grams of malonic acid having the structure:

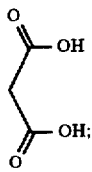

700 grams of triethyl amine. With stirring, the reaction mass heated to 90° C. and maintained at 90° C. for a period of 15.5 hours.

At the end of the 15.5 hour period, the reaction mass is cooled to 27°–30° C. and 750 grams of a 50% sodium hydroxide solution is added to the reaction mass causing the pH of the reaction mass to be at approximately 12.

300 Grams of water is then added to the reaction mass.

The reaction mass is stripped of solvent at 50° C. and 50 mm/Hg. pressure. 852 Grams of distillate are removed. The remaning product is then acidified using 622 grams of concentrated hydrochloric acid to a pH of 1.5.

The resulting reaction mass now exists in two phases: an organic phase and an aqueous phase.

170 Grams of the resulting carboxylic acid is admixed with 170 grams of allyl alcohol. The resulting mixture is then heated with stirring to 160° C. and maintained at 160° C. for a period of 11 hours.

At the end of the 11 hour period, the reaction product is filtered and distilled yielding the following fractions:

| Fraction Number | Vapor Temperature (°C.) | Liquid Temperature (°C.) | Vacuum mm/Hg. Pressure | Weight of Fraction |
|---|---|---|---|---|
| 1 | 64/88 | 128/129 | 1.6/1.6 | 13.6 |
| 2 | 96 | 130 | 2.4 | 12.0 |
| 3 | 97 | 130 | 2.4 | 13.5 |
| 4 | 98 | 131 | 2.4 | 13.1 |
| 5 | 99 | 130 | 2.4 | 13.3 |
| 6 | 100 | 131 | 2.4 | 13.1 |
| 7 | 77 | 128 | 0.8 | 13.5 |
| 8 | 77 | 128 | 0.8 | 10.3 |
| 9 | 77 | 130 | 0.8 | 8.3 |
| 10 | 77 | 139 | 0.8 | 9.6 |
| 11 | 80 | 156 | 0.9 | 4.3 |
| 12 | — | 200 | 1.1 | 6.6 |

It should be noted that the peaks on the GC spectrum of FIG. 10 indicated by reference numeral 102 are for isomers of a lactone having the structure:

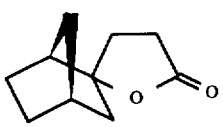

with the desired products peak indicated by reference numeral 101 (having the structure:

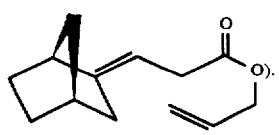

23

The amount of lactone having the structure:

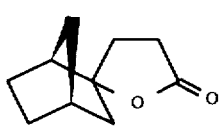

can be diminished if instead of carrying out the reaction:

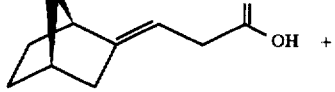 +

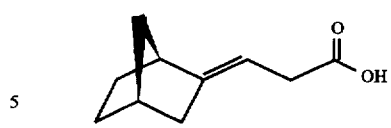

is first esterified as with dimethyl sulfate, methyl alcohol (in the presence of a sulfuric acid catalyst or methyl iodide).

EXAMPLE IV

Production of 2-Dehydronorbornylidene Propionic Acid, Allyl Ester

Reactions:

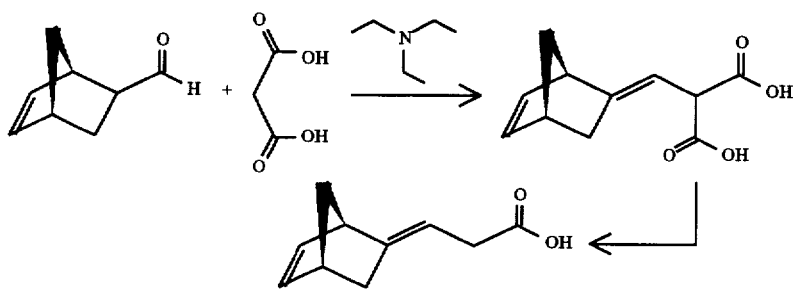

and

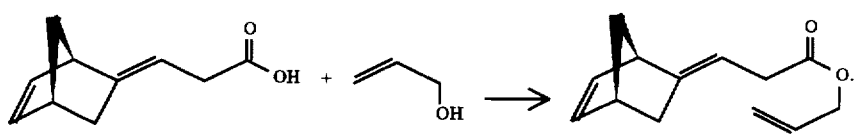

-continued

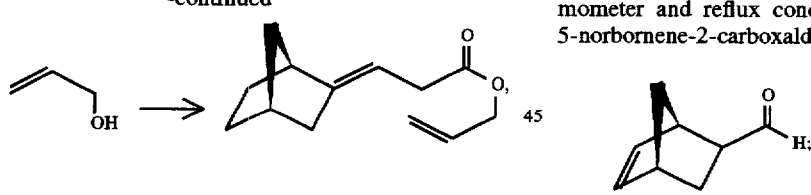

the reaction:

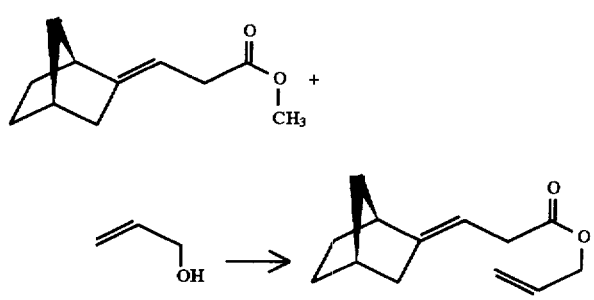

is carried out whereby the carboxylic acid having the structure:

Into a 2 liter reaction vessel equipped with stirrer, thermometer and reflux condenser are placed 200 grams of 5-norbornene-2-carboxaldehyde having the structure:

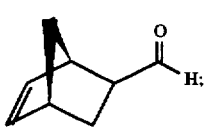

250 grams of malonic acid having the structure:

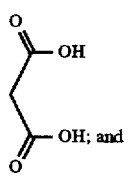

560 grams of triethyl amine. With stirring, the reaction mass is heated to 88° C. and maintained at 88° C. (reflux conditions) for a period of 17 hours.

At the end of the 17 hour period, the reaction mass is cooled to 32°–35° C.

A 10% aqueous sodium hydroxide solution is then added to the reaction mass (640 grams) causing the reaction mass pH to be at 9. An additional 20% aqueous sodium hydroxide mixture (120 grams) is then added to the reaction mass to bring the reaction mass to a pH of 12.

The triethyl amine catalyst is then stripped from the reaction mass at 100 mm/Hg. until 660 grams of distillate was removed.

The remainder of the reaction mass is then extracted with three 150 gram portions of toluene and then acidified using 316 grams of concentrated hydrochloric acid.

The reaction mass now exists in two phases: an organic phase and an aqueous phase. The organic phase is the lower phase weighing 350 grams. The upper phase is the acid phase weighing 1,429 grams.

The organic phase is admixed with 150 grams of allyl alcohol and the resulting mixture is heated to 160° C. and maintained at 160° C. for a period of 7 hours. NMR, IR and mass spectral analysis yield the information that the resulting product has the structure:

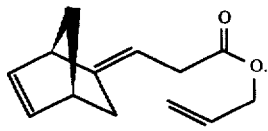

The resulting product is distilled on a ten-plate Vigreux column yielding the following fractions:

| Fraction Number | Vapor Temperature (°C.) | Liquid Temperature (°C.) | Vacuum mm/Hg. Pressure | Weight of Fraction |
|---|---|---|---|---|
| 1 | 25/91 | 125/130 | 1.4 | 4.5 |
| 2 | 89 | 120 | 1.2 | 5.6 |
| 3 | 87 | 119 | 1.1 | 9.6 |
| 4 | 83 | 120 | 0.8 | 10.8 |
| 5 | 83 | 121 | 0.8 | 13.6 |
| 6 | 83 | 123 | 0.8 | 8.6 |
| 7 | 83 | 118 | 0.8 | 13.0 |
| 8 | 83 | 118 | 0.8 | 15.5 |
| 9 | 83 | 115 | 0.7 | 15.5 |
| 10 | 75 | 154 | 0.7 | 8.1 |
| 11 | 88 | 200 | 0.7 | 3.3 |

EXAMPLE V

Preparation of Floral Fragrance

The following mixture is prepared:

| Ingredients | V(A) | V(B) | V(C) | V(D) |
|---|---|---|---|---|
| Hydroxcitronellal | 22% | 22% | 22% | 22% |
| Phenyl Ethyl Alcohol | 12% | 12% | 12% | 12% |
| Heliotropine | 12% | 12% | 12% | 12% |
| Linalool | 8% | 8% | 8% | 8% |
| Cinnamic Alcohol | 4% | 4% | 4% | 4% |
| Indole (10% in Diethyl Phthalate) | 2% | 2% | 2% | 2% |
| Benzyl Acetate | 8% | 8% | 8% | 8% |
| Anisic Alcohol | 8% | 8% | 8% | 8% |
| Coumarin (10% in Diethyl Phthalate) | 4% | 4% | 4% | 4% |
| The compound having the structure: | 4% | 0% | 0% | 0% |

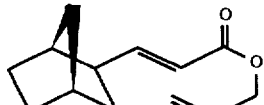

(prepared according to Example I(B))

| Ingredients | V(A) | V(B) | V(C) | V(D) |
|---|---|---|---|---|
| bulked distillation Fractions 7–20). The compound having the structure: | 0% | 4% | 0% | 0% |

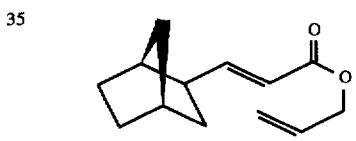

prepared according to Example II.
The compound having the structure: 0%  0%  4%  0% prepared according to Example III
distillation Fraction 6.
The compound having the structure: 0%  0%  0%  4%

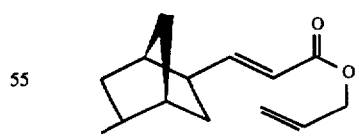

prepared according to Example IV
bulked distillation Fractions 5–10.

When the compound having the structure:

is added to this floral fragrance, the floral fragrance achieves coconut, pineapple-like, fruity and lactonic undertones with pineapple and galbanum topnotes. Accordingly, the fragrance of Example V(A) can be described as:

"A floral aroma with coconut, pineapple-like, fruity and lactonic undertones and pineapple and galbanum topnotes."

When the compound having the structure:

is added to this floral fragrance, the floral fragrance gains coumarin-like and lactonic undertones with sweet, herbaceous and oolong tea-like topnotes. Accordingly, the fragrance of Example V(B) can be described as:

"A floral aroma with coumarin-like and lactonic undertones and sweet, herbaceous and oolong tea-like topnotes."

When the compound having the structure:

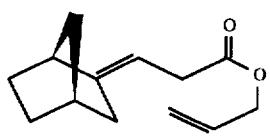

is added to this floral fragrance, the floral fragrance attains sweet, animalic, fruity and pineapple undertones with galbanum, sweaty and animalic topnotes. Accordingly, the fragrance of Example V(C) can be described as:

"A floral aroma with sweaty, animalic, fruity and pineapple undertones and galbanum, sweaty and animalic topnotes."

When the compound having the structure:

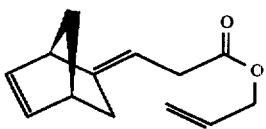

is added to this floral fragrance formulation, the floral fragrance formulation gains sweaty and animalic undertones and coconut, sweaty and animalic topnotes. Accordingly, the fragrance of Example V(D) can be described as:

"A floral aroma having sweaty and animalic undertones and coconut, sweaty and animalic topnotes."

EXAMPLE VI

Preparation of Cosmetic Powder Compositions

Cosmetic powder compositions are prepared by mixing in a ball mill 100 grams of talcum powder with 0.25 grams of each of the substances set forth in Table II below. Each of the cosmetic powder compositions has an excellent aroma as described in Table II below:

TABLE II

| Substance | Aroma Description |
|---|---|
| The compound having the structure: ![] prepared according to Example I(B) bulked distillation Fractions 7–20. | A coconut, pineapple-like, fruity and lactonic aroma with pineapple and galbanum topnotes and floral undertones. |
| The compound having the structure: ![] prepared according to Example II. | A coumarin-like, lactonic aroma with sweet, herbaceous and oolong tea-like topnotes. |
| The compound having the structure: | A sweaty, animalic, fruity and pineapple aroma with galbanum, |

TABLE II-continued

| Substance | Aroma Description |
|---|---|
| ![] prepared according to Example III distillation Fraction 6. The compound having the structure: ![] prepared according to Example IV bulked distillation Fractions 5–10. | sweaty and animalic topnotes. A sweaty, animalic aroma with coconut, sweaty and animalic topnotes. |
| Perfume composition of Example V(A). | A floral aroma with coconut, pineapple-like, fruity and lactonic undertones and pineapple and galbanum topnotes. |
| Perfume composition of Example V(B) | A floral aroma with coumarin-like and lactonic undertones and sweet, herbaceous and oolong tea-like topnotes. |
| Perfume composition of Example V(C). | A floral aroma with sweaty, animalic, fruity and pineapple undertones and galbanum, sweaty and animalic topnotes. |
| Perfume composition of Example V(D). | A floral aroma having sweaty and animalic undertones and coconut, sweaty and animalic topnotes. |

EXAMPLE VII

Perfumed Liquid Detergent

Concentrated liquid detergents with aromas as set forth in Table II of Example VI (which detergents are prepared from Lysine sale of n-dodecyl benzene sulfonic acid as more specifically described in U.S. Pat. No. 3,948,818 issued on Apr. 6, 1976 the specification for which is incorporated by reference herein) are prepared containing each of the substances set forth in Table II of Example VI, supra. They are prepared by adding and homogeneously mixing the appropriate quantity of perfumery substance as set forth in Table II of Example VI in the liquid detergent. The detergents all possess aromas as set forth in Table II of Example VI, the intensity increasing with greater concentrations of perfumery substance of Table II of Example VI, supra.

EXAMPLE VIII

Preparation of a Cologne and Handkerchief Perfume

The perfume substances of Table II of Example VI, supra, are incorporated into colognes at concentrations of 1.5%, 2.0%, 2.5%, 3.0% and 4.0% in 80%, 85% and 90% aqueous ethanols; and into a handkerchief perfume composition at concentrations of 10%, 15%, 20%, 25% and 30% (in 85%, 90% and 95% aqueous ethanols. Distinct and definitive aromas as set forth in Table II of Example VI are imparted to the cologne and to the handkerchief perfume compositions.

EXAMPLE IX

Preparation of a Detergent Composition

A total of 100 grams of a detergent powder (a nonionic detergent powder containing a proteolytic enzyme prepared according to Example I of Canadian Letters Patent No. 985,190 issued on Mar. 9, 1976 the disclosure of which is incorporated by reference herein) is mixed with 0.15 grams of each of the substances set forth in Table II of Example VI, supra, until substantially homogeneous compositions are obtained. These compositions have excellent aromas as set forth in Table II of Example VI.

EXAMPLE X

Preparation of Soap

Each of the perfumery substances of Table II of Example VI are incorporated into soap (LVU-1) at 0.1% by weight of each substance. After two weeks in the oven at 90° F., each of the soaps showed no visual effect from the heat. Each of the soaps manifested an excellent aroma as set forth in Table II of Example VI, supra.

EXAMPLE XI

Preparation of Soap Composition

100 Grams of soap chips (IVORY®, Registered Trademark of the Procter & Gamble Company of Cincinnati, Ohio) are mixed individually with one gram each of the perfumery substances of Table II of Example VI, supra, until a homogeneous composition is obtained. The homogeneous composition is then treated under 3 atmospheres pressure at 180° C. for a period of 3 hours and the resulting liquid is placed into a soap mold. The resulting soap cakes, on cooling, manifest excellent aromas as set forth in Table II of Example VI, supra.

EXAMPLE XII

Preparation of a Solid Detergent Composition

A detergent is prepared from the following ingredients according to Example I of Canadian Letters Patent No. 1,007,948 (the specification for which is incorporated by reference herein):

| Ingredients | Parts by Weight |
| --- | --- |
| "Neodol 45-11" (a $C_{14}$—$C_{15}$ alcohol ethoxylated with 11 moles of ethylene oxide) | 12 |
| Sodium carbonate | 55 |
| Sodium citrate | 20 |
| Sodium sulfate, water brighteners | q.s. |

This detergent is a "phosphate-free" detergent. A total of 100 grams of this detergent is admixed separately with 0.15 grams of each of the perfume substances of Table II of Example VI, supra. The detergent samples each have excellent aromas as set forth in Table II of Example VI, supra.

EXAMPLE XIII

Utilizing the procedure of Example I at column 15 of U.S. Pat. No. 3,632,396 (the specification for which is incorporated by reference herein), a non-woven cloth substrate useful as a dryer-added fabric softening article of manufacture is prepared, wherein the substrate, the substrate coating and the outer coating and the perfuming material are as follows:

1. a water "dissolvable" paper ("Dissolvo Paper");
2. Adogen 448 (m.p. about 140° F.) as the substrate coating; and
3. an outer coating having the following formulation (m.p. about 150° F.);

57% $C_{20-22}$HAPS;

22% isopropyl alcohol;

20% antistatic agent; and

1% of one of the perfume substances of Table II of Example VI, supra.

A fabric softening composition prepared as set forth above having the above aroma characteristics as set forth in Table II of Example VI, supra, essentially consists of a substrate having a weight of about 3 grams per 100 square inches, a substrate coating of about 1.85 grams per 100 square inches of substrate and an outer coating of about 1.4 grams per 100 square inches of substrate, thereby providing a total aromatized substrate and outer coating weight ratio of about 1:1 by weight of substrate. The aroma set forth in Table II of Example VI is imparted in a pleasant manner to the headspace in the dryer on operation thereof, using said dryer-added fabric softening non-woven fabric.

EXAMPLE XIV

Preparation of Soap Composition

100 Grams of soap chips (IVORY®, Registered Trademark of the Procter & Gamble Company of Cincinnati, Ohio) are mixed with 2 grams of a 50:50 mixture of the compound having the structure:

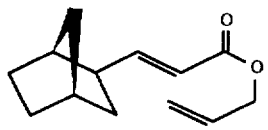

prepared according to Example I(A) and the compound having the structure:

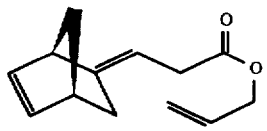

prepared according to Example IV until a homogeneous composition is obtained. The homogeneous composition is then treated under 3 atmospheres pressure at 180° C. for a period of 3 hours and the resulting liquid is placed into a soap mold. The resulting soap cakes on cooling manifest an aroma which can be described as "coconut, pineapple-like, fruity, lactonic, sweaty and animalic with pineapple, galbanum, coconut, sweaty and animalic topnotes and floral undertones".

What is claimed is:

1. A process for preparing an allyl ester defined according to the structure:

31

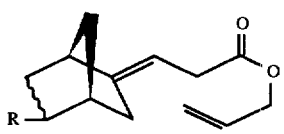

wherein the wavy line represents a carbon-carbon single bond or a carbon-carbon double bond; and wherein R represents methyl or hydrogen, comprising the steps of:

(i) reacting malonic acid having the structure:

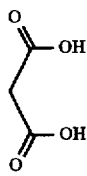

with the aldehyde having the structure:

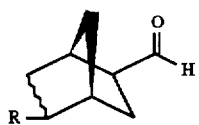

in the presence of the catalyst having the structure:

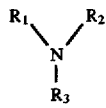

wherein $R_1$, $R_2$ and $R_3$ are the same or different $C_1$–$C_3$ alkyl at a temperature of 90° C. in accordance with the reaction:

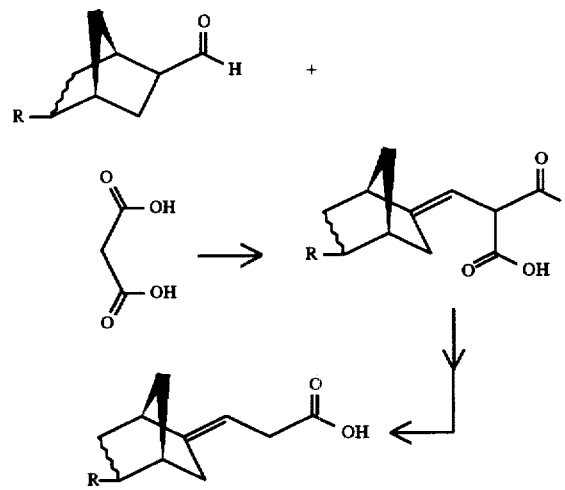

32 whereby the compound having the structure:

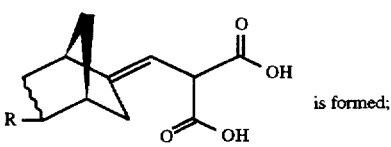

is formed;

(ii) then decarboxylating the resulting compound having the structure:

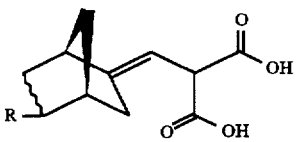

to form the compound having the structure:

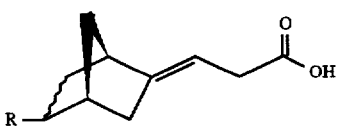

by raising the pH of the reaction mass to approximately 12 and then lowering it to approximately 1.5; and (iii) then esterifying the resultant compound having the structure:

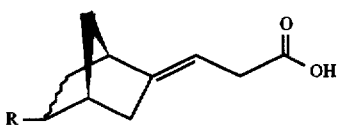

by means of either:

(a) reacting the compound having the structure:

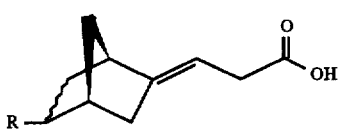

with allyl alcohol according to the reaction:

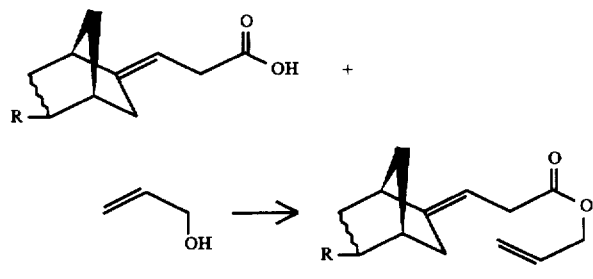

in the presence of an acid catalyst selected from the group consisting of methane sulfonic acid and an acid ion exchange resin catalyst at atmospheric pressure at a temperature in the range of from about 150° C. up to about 170° C. for a period of time of from about 10 hours up to about 15 hours; or (b) reacting the compound having the structure:

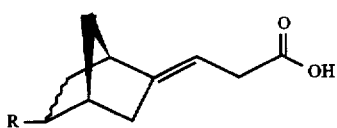

with the esterification reagent having the formula:

[R']Z wherein R' is $C_1$–$C_5$ alkyl and Z is selected from the group consisting of hydroxyl, iodide and sulfate according to the reaction:

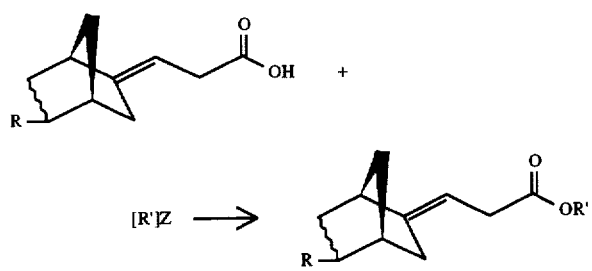

whereby the compound having the structure:

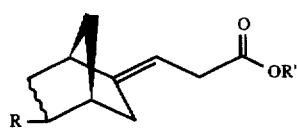

is formed; and then reacting the resulting compound having the structure:

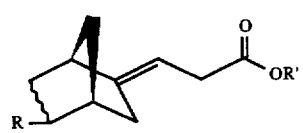

with allyl alcohol according to the reaction:

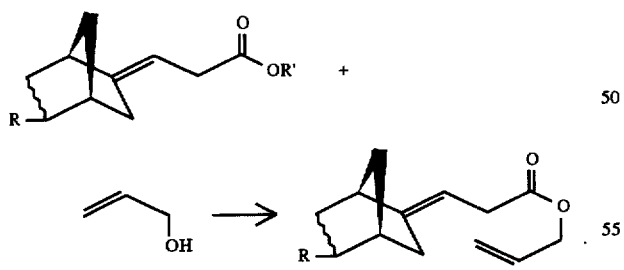

2. A process for preparing an allyl ester defined according to the structure:

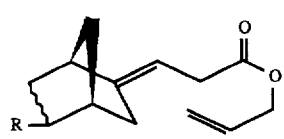

wherein the wavy line represents a carbon-carbon single bond or a carbon-carbon double bond; and wherein R represents methyl or hydrogen, comprising the steps of:

(i) reacting malonic acid having the structure:

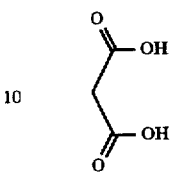

with the aldehyde having the structure:

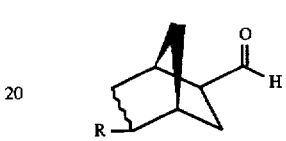

in the presence of a mixed pyridine and piperidine catalyst at a temperature of 90° C. in accordance with the reaction:

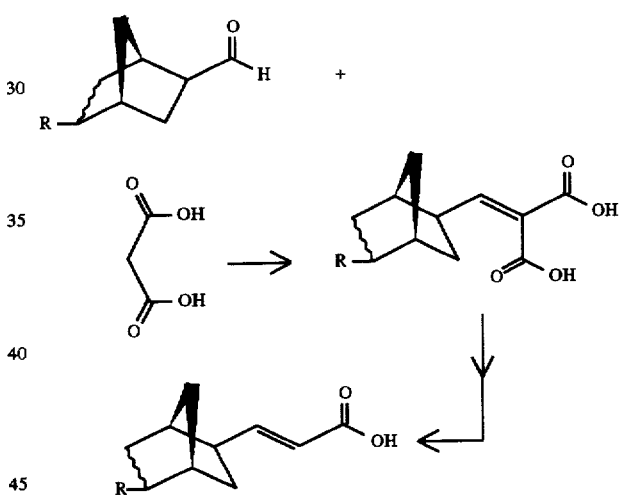

whereby the compound having the structure:

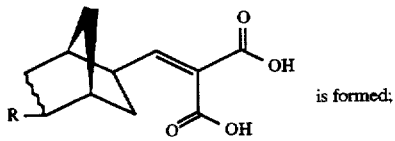

is formed;

(ii) then decarboxylating the resulting compound having the structure:

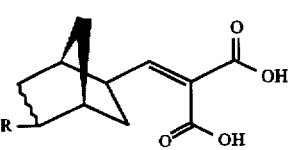

to form the compound having the structure:

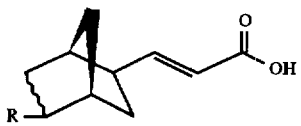

by raising the pH of the reaction mass to a range of from 11 up to 11.5 and then reducing the pH of the reaction mass to a pH of about 1 while heating the reaction mass; and (iii) then esterifying the resultant compound having the structure:

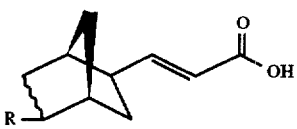

by means of either:

(a) reacting the compound having the structure:

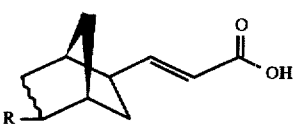

with allyl alcohol according to the reaction:

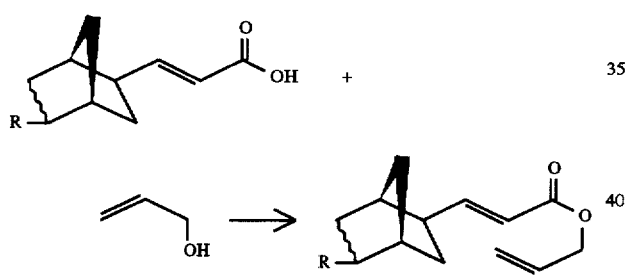

in the presence of an acid catalyst selected from the group consisting of methane sulfonic acid and an acid ion exchange resin catalyst at atmospheric pressure at a temperature in the range of from about 150° C. up to about 170° C. for a period of time of from about 10 hours up to about 15 hours; or (b) reacting the compound having the structure:

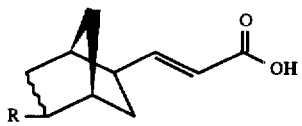

with the esterification reagent having the formula:

[R']Z wherein R' is $C_1$–$C_5$ alkyl and Z is selected from the group consisting of hydroxyl, iodide and sulfate according to the reaction:

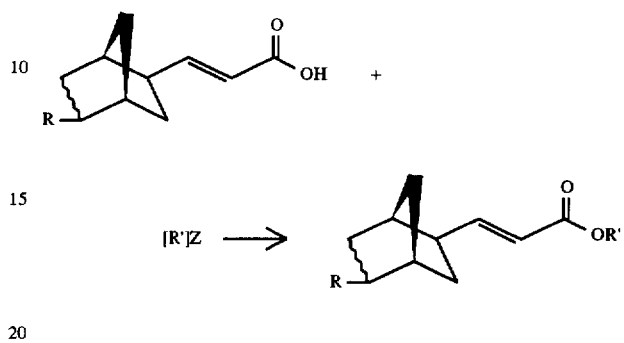

whereby the compound having the structure:

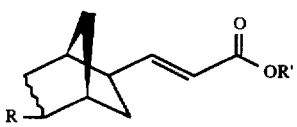

is formed; and then reacting the resulting compound having the structure:

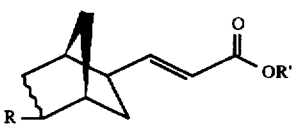

with allyl alcohol according to the reaction:

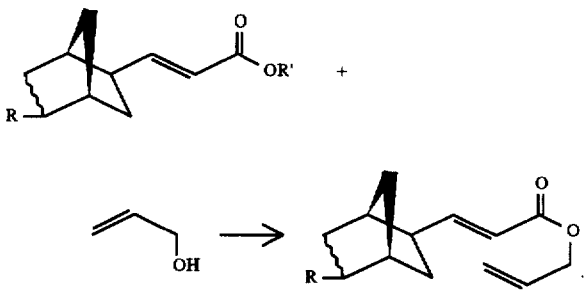

* * * * *